(12) United States Patent
Buschmann et al.

(10) Patent No.: US 11,311,012 B1
(45) Date of Patent: *Apr. 26, 2022

(54) BACTERIAL CONTROL IN FERMENTATION SYSTEMS

(71) Applicant: Clean Chemistry, Inc., Boulder, CO (US)

(72) Inventors: Wayne E. Buschmann, Boulder, CO (US); Carl R. Evenson, Erie, CO (US)

(73) Assignee: Clean Chemistry, Inc., Boulder, CO (US)

( * ) Notice: Subject to any disclaimer, the term of this patent is extended or adjusted under 35 U.S.C. 154(b) by 181 days.

This patent is subject to a terminal disclaimer.

(21) Appl. No.: 16/394,971

(22) Filed: Apr. 25, 2019

Related U.S. Application Data

(63) Continuation-in-part of application No. 16/125,431, filed on Sep. 7, 2018, now Pat. No. 11,001,864.

(60) Provisional application No. 62/555,405, filed on Sep. 7, 2017.

(51) Int. Cl.
*A01N 37/16* (2006.01)
*C12P 7/06* (2006.01)

(52) U.S. Cl.
CPC ............... *A01N 37/16* (2013.01); *C12P 7/06* (2013.01)

(58) Field of Classification Search
CPC .................................. A01N 37/16; C12P 7/06
See application file for complete search history.

(56) References Cited

U.S. PATENT DOCUMENTS

| | | | |
|---|---|---|---|
| 3,719,552 A | 3/1973 | Farley | |
| 3,925,234 A | 12/1975 | Hachmann et al. | |
| 4,055,505 A | 10/1977 | Gray | |
| 4,076,621 A | 2/1978 | Hardison | |
| 4,348,256 A | 9/1982 | Bergstrom, Jr. et al. | |
| 4,393,037 A | 7/1983 | Delaney | |
| 4,576,609 A | 3/1986 | Hageman | |
| 4,673,473 A | 6/1987 | Ang | |

(Continued)

FOREIGN PATENT DOCUMENTS

| | | |
|---|---|---|
| CN | 1142555 | 2/1997 |
| CN | 102007230 | 4/2011 |

(Continued)

OTHER PUBLICATIONS

U.S. Appl. No. 16/798,132, entitled "Systems and Methods for Generation of Reactive Oxygen Species and Applications Thereof", filed Feb. 21, 2020.

(Continued)

*Primary Examiner* — Katherine D Leblanc

(74) *Attorney, Agent, or Firm* — Snell & Wilmer L.L.P.

(57) ABSTRACT

In some embodiments, methods of controlling microbial contamination in fermenters, feedstocks and water, which is deleterious to fermentation, involving the use of peracetate oxidant solutions designed to generate reactive oxygen species. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1.

12 Claims, 7 Drawing Sheets

(56) References Cited

U.S. PATENT DOCUMENTS

| | | |
|---|---|---|
| 4,722,773 A | 2/1988 | Plowman et al. |
| 4,952,276 A | 8/1990 | Gidlund |
| 4,966,706 A | 10/1990 | Gregor |
| 5,053,142 A | 10/1991 | Sorensen et al. |
| 5,246,543 A | 9/1993 | Meier et al. |
| 5,387,317 A | 2/1995 | Parthasarathy et al. |
| 5,424,032 A | 6/1995 | Christensen et al. |
| 5,431,781 A | 7/1995 | Walsh |
| 5,472,619 A | 12/1995 | Holzhauer et al. |
| 5,494,588 A | 2/1996 | LaZonby |
| 5,565,073 A | 10/1996 | Fraser et al. |
| 5,683,724 A | 11/1997 | Hei et al. |
| 5,770,035 A | 6/1998 | Faita |
| 5,785,812 A | 7/1998 | Linsten et al. |
| 5,817,240 A | 10/1998 | Miller et al. |
| 6,007,678 A | 12/1999 | Linsten et al. |
| 6,015,536 A | 1/2000 | Lokkesmoe et al. |
| 6,126,782 A | 10/2000 | Liden et al. |
| 6,183,623 B1 | 2/2001 | Cisar et al. |
| 6,258,207 B1 | 7/2001 | Pan |
| 6,387,238 B1 | 5/2002 | Merk et al. |
| 6,569,286 B1 | 5/2003 | Withenshaw et al. |
| 6,712,949 B2 | 3/2004 | Gopal |
| 8,318,972 B2 | 11/2012 | Buschmann et al. |
| 9,517,955 B2 | 12/2016 | Buschmann |
| 9,517,956 B2 | 12/2016 | Buschmann |
| 9,551,076 B2 | 1/2017 | Buschmann |
| 10,259,729 B2 | 4/2019 | Buschmann |
| 10,472,265 B2 | 11/2019 | Buschmann |
| 10,501,346 B2 | 12/2019 | Buschmann |
| 10,577,698 B2 | 3/2020 | Buschmann |
| 10,611,656 B2 | 4/2020 | Buschmann |
| 10,875,798 B2 | 12/2020 | Buschmann |
| 10,875,799 B2 | 12/2020 | Buschmann |
| 10,883,224 B2 | 1/2021 | Buschmann |
| 10,941,063 B2 | 3/2021 | Buschmann |
| 2001/0050234 A1 | 12/2001 | Shiepe |
| 2002/0153262 A1 | 10/2002 | Uno et al. |
| 2003/0019757 A1 | 1/2003 | Vetrovec |
| 2003/0019758 A1 | 1/2003 | Gopal |
| 2003/0024054 A1 | 2/2003 | Burns |
| 2004/0112555 A1 | 6/2004 | Tolan et al. |
| 2004/0134857 A1 | 7/2004 | Huling et al. |
| 2004/0200588 A1 | 10/2004 | Walker |
| 2005/0183949 A1 | 8/2005 | Daly |
| 2006/0207734 A1 | 9/2006 | Day |
| 2007/0074975 A1 | 4/2007 | Buschmann et al. |
| 2007/0212594 A1 | 9/2007 | Takasu et al. |
| 2007/0243449 A1 | 10/2007 | Sotomura et al. |
| 2009/0012346 A1 | 1/2009 | Al Nashef et al. |
| 2009/0090478 A1 | 4/2009 | Hollomon et al. |
| 2009/0152123 A1 | 6/2009 | Butler et al. |
| 2009/0285738 A1 | 11/2009 | Winter et al. |
| 2009/0314652 A1 | 12/2009 | Buschmann |
| 2010/0078331 A1 | 4/2010 | Scherson et al. |
| 2010/0160449 A1 | 6/2010 | Rovison, Jr. et al. |
| 2010/0176066 A1 | 7/2010 | Budde et al. |
| 2010/0179368 A1 | 7/2010 | Conrad |
| 2011/0017066 A1 | 1/2011 | Takeuchi et al. |
| 2011/0024361 A1 | 2/2011 | Schwartzel |
| 2011/0123642 A1 | 5/2011 | Wilmotte |
| 2011/0232853 A1 | 9/2011 | Yin |
| 2012/0067532 A1 | 3/2012 | Lee |
| 2012/0091069 A1 | 4/2012 | Fischmann |
| 2012/0108878 A1 | 5/2012 | Conrad |
| 2012/0145643 A1 | 6/2012 | Pandya |
| 2012/0240647 A1 | 9/2012 | Montemurro |
| 2012/0267315 A1 | 10/2012 | Soane et al. |
| 2012/0322873 A1 | 12/2012 | Atkins et al. |
| 2013/0259743 A1 | 10/2013 | Keasler et al. |
| 2013/0264293 A1 | 10/2013 | Keasler et al. |
| 2014/0069821 A1 | 3/2014 | Marcin et al. |
| 2014/0072653 A1 | 3/2014 | Buschmann |
| 2014/0131217 A1 | 5/2014 | Buschmann |
| 2014/0131259 A1 | 5/2014 | Goldblatt |
| 2014/0197102 A1 | 7/2014 | Van Der Wal et al. |
| 2014/0205777 A1 | 7/2014 | Hawkins et al. |
| 2014/0238626 A1 | 8/2014 | Tsuji et al. |
| 2014/0374104 A1 | 12/2014 | Seth |
| 2016/0068417 A1 | 3/2016 | Buschmann |
| 2016/0297697 A1 | 10/2016 | Buschmann |
| 2016/0318778 A1 | 11/2016 | Buschmann |
| 2017/0051417 A1 | 2/2017 | Buschmann |
| 2017/0107128 A1 | 4/2017 | Buschmann |
| 2017/0114468 A1 | 4/2017 | Buschmann |
| 2017/0158537 A1 | 6/2017 | Buschmann |
| 2017/0159237 A1 | 6/2017 | Buschmann |
| 2017/0335515 A1 | 11/2017 | Buschmann |
| 2018/0023250 A1 | 1/2018 | Buschmann |
| 2019/0031545 A1 | 1/2019 | Buschmann et al. |
| 2019/0218121 A1 | 7/2019 | Buschmann |
| 2020/0062623 A1 | 2/2020 | Buschmann |
| 2020/0079665 A1 | 3/2020 | Buschmann |
| 2020/0199000 A1 | 6/2020 | Buschmann |
| 2020/0262725 A1 | 8/2020 | Buschmann |

FOREIGN PATENT DOCUMENTS

| | | |
|---|---|---|
| EP | 480469 A3 | 4/1992 |
| WO | 9402423 A1 | 2/1994 |
| WO | 9739179 A1 | 10/1997 |
| WO | 1999032710 | 7/1999 |
| WO | 2000069778 | 11/2000 |
| WO | 2008056025 A2 | 5/2008 |
| WO | 2010059459 | 5/2010 |
| WO | 2012166997 | 12/2012 |
| WO | 2013060700 A1 | 5/2013 |
| WO | 2013064484 | 5/2013 |
| WO | 2014039929 | 3/2014 |
| WO | 2014100828 | 6/2014 |
| WO | 2016037149 | 3/2016 |
| WO | 2016154531 | 9/2016 |
| WO | 2017100284 | 6/2017 |
| WO | 2017100299 | 6/2017 |
| WO | 2018106285 | 6/2018 |

OTHER PUBLICATIONS

U.S. Appl. No. 17/222,704, entitled "Systems and Methods for Generation of Reactive Oxygen Species and Applications Thereof", filed Apr. 5, 2021.

U.S. Appl. No. 17/119,956, entitled "Systems and Method for Oxidative Treatment Utilizing Reactive Oxygen Species and Appications Thereof", filed Dec. 11, 2020.

U.S. Appl. No. 16/806,148, entitled "Methods of Paper Mill Processign Using Recycled White Water With Microbial Control", filed Mar. 2, 2020.

U.S. Appl. No. 17/133,261, entitled "Methods of Pulp Fiber Treatment", filed Dec. 23, 2020.

Smook, Handbook for Pulp & Paper Technologists, 1992, Chapter 4: Overview of Pulping Methodology and Chapter 7: Kraft Pulping, Fifth printing 2001, Angus Wilde Publications, Vancouver B.C., pp. 36-44 and 74-83.

Suihko et al.; "A study of the microflora of some recyled fibre pulps, boards and kitchen rolls"; The Journal of Applied Microbiology; 1997; vol. 83; pp. 199-207.

Shackford; "A Comparison of Pulping and Bleaching of Kraft Softwood and Eucalyptus Pulps"; 36th Intl. Pulp and Paper Congress and Exhibition; Oct. 13-16, 2003; Sao Paulo, Brazil; 17 pgs.

Suslow; "Oxidation-Reduction Potential (ORP) for Water Disinfection Monitoring, Control, and Documentation"; Univ. California; Division of Agriculture and Natural Resources; ANR Publication 8149; 5 pgs.; http://anrcatalog.ucdavis.edu; 2004; 5 pgs.

Pedros et al.; "Chlorophyll fluorescence emission spectrum inside a leaf"; The Royal Society of Chemistry and Owner Societies; 2008; No. 7; pp. 498.

Coyle et al.; "Peracetic Acid as an Alternative Disinfection Technology for Wet Weather Flows"; Water Environment Research; Aug. 2014; pp. 687-697.

(56) References Cited

OTHER PUBLICATIONS

Smook; Chapter 14: Secondary Fiber;Handbook for Pulp & Papers Technologists; Angus Wilde Publications; 2001; pp. 209-219.

Gullichsen et al., eds.; Chemical Pulping; Papermaking Science and Technology; Book 6A; 1999; Fapet Oy; pp. A40-A41 and A616-A665.

Hill et al.; "Part 1: Peracetic Acid—An effective alternative for Chlorine compound Free Delignification of Kraft Pulp"; 1992; Pulping Conference; pp. 1219-1230.

Verween et al.; "Comparative toxicity of chlorine and peracetic acid in the biofouling control of Mytilopsis leucophaeata and Dreissena polymorpha embryos (Mollusca, Bivalvia)"; International Biodeterioration & Biodegradation; vol. 63, No. 4; 2009; pp. 523-528.

U.S. Appl. No. 15/334,012 entitled "Electrochemical Reactor and Process".

U.S. Appl. No. 15/308,966 entitled "System and Method for Generation of Reactive Oxygen Species and Applications Thereof".

U.S. Appl. No. 15/371,567 entitled "Methods of Microbial Control".

U.S. Appl. No. 15/601,350 entitled "Methods of Pulp Fiber Treatment".

U.S. Appl. No. 15/658,709 entitled "Methods of Optical Brightening Agent Removal".

U.S. Appl. No. 16/125,431 entitled "Bacterial Control in Fermentation Systems".

U.S. Appl. No. 16/148,222 entitled "Methods of Pulp Fiber Treatment".

U.S. Appl. No. 16/363,819 entitled "Systems and Method for Oxidative Treatment Utilizing Reactive Oxygen Species and Applications Thereof".

U.S. Appl. No. 16/667,549 entitled "Systems and Methods of Reducing a Bacteria Population in High Hydrogen Sulfide Water".

U.S. Appl. No. 16/681,482 entitled "System and Method for Generation of Point of Use Reactive Oxygen Species".

BACTERIAL CONTROL IN FERMENTATION SYSTEMS

CROSS-REFERENCE

This application is a continuation-in-part of U.S. patent application Ser. No. 16/125,431 entitled BACTERIAL CONTROL IN FERMENTATION SYSTEMS filed on Sep. 7, 2018, which claims the benefit of U.S. provisional patent application No. 62/555,405 entitled METHODS OF MICROBIAL CONTROL IN FERMENTATION PROCESSES filed on Sep. 7, 2017, the entire contents of which are each incorporated herein by reference for all purposes.

BACKGROUND OF THE INVENTION

1. Field of the Invention

The present disclosure generally relates to microbial control in fermentation processes using peracetate oxidant solutions designed to generate reactive oxygen species. The disclosure more particularly relates to methods of reducing microbial contamination in fermenters, feedstocks and water, which is deleterious to fermentation, involving the use of peracetate oxidant solutions designed to generate reactive oxygen species.

2. Description of the Relevant Art

Contamination of fermentation processes by bacteria, biofilms and pathogenic fungi reduces the efficiency of fermentation processes and produces undesirable byproducts or contaminants. Fermentation processes using yeast to produce alcohols, including ethanol, are subject to bacterial infections which reduce production efficiency and yield. For example, infections of *Lactobacillus* and *Acetobacter* consume sugars producing organic acids, which reduces sugar conversion to alcohol and inhibit yeast activity. Reduced fermentation efficiency from bacteria contamination results in significant financial losses to bioethanol and biochemical production industries. Reduced fermentation efficiency also reduces the greenhouse gas savings over petroleum-based gasoline.

Control of bacteria in fermentation processes is most often achieved with the use of antibiotics, oxidizing biocides and non-oxidizing biocides or bactericidal agents, generally categorized as "processing aids." Bactericidal agents are typically added to the fermentation mixture or grist to selectively reduce the bacteria population while having little to no impact on the yeast, which remain active. Bactericidal agents also need to be compatible and effective in the presence of high organic material concentrations. These bacteria control methods are common practice in fuel ethanol industry and processes relying on fermentation with yeast.

The increased use of spent fermented sugar sources from ethanol fuel production for animal feed has increased the demand and regulations for eliminating potentially harmful residues from these materials. The residuals of antibacterial treatments used as processing aids are of particular concern when the byproducts of the distillation process including spent grist, stillage or distillers dried grains with solubles (DDGS) are converted to animal feed. The presence of antibiotics and toxic byproducts are becoming unacceptable in feed products over concerns of antibiotic resistance and toxic materials spreading through animal feed operations.

Antibiotics currently dominate the market bacteria control and include virginiamycin, penicillin, and erythromycin. These products are generally inexpensive, but lead to buildup of resistant populations in fermenters and some residues can be persistent in DDGS. Antibiotic-free DDGS is in increasing demand, particularly in poultry feed.

Oxidizing biocides are generally fast-acting, but can create undesirable and toxic byproducts and increase corrosion of process equipment and heat exchangers. In some cases, the oxidizing biocide chemistry may alter the fermentation process conditions. Products commonly used include chlorine dioxide and peracetic acid, which are fast acting and can control biofilm growth in equipment. Both products are acidic and use of elevated concentrations can have pH impacts. Byproducts of chlorine dioxide include chlorate (regulated as a toxic oxidant byproduct in drinking water) and, in the presence of reactive organic materials including lignin in plants, toxic chlorinated phenols and furans. Chlorine dioxide products in water generally increase corrosion rates in process equipment. Peracetic acid is often used at higher concentrations than chlorine dioxide and can add significant amounts of acetic acid and hydrogen peroxide to fermentation processes, which can result in yeast inhibition.

Non-oxidizing biocide residuals can be less toxic and less corrosive than strong oxidizers, but they are typically much slower to provide bacteria control and are often significantly more expensive and more persistent over time than oxidizers. Low-toxicity, non-oxidizing biocides do not have the bactericidal capacity to rapidly treat a contaminated fermenter and often do not have the capacity to reduce bacteria populations that have gotten out of control or reside in biofilms in heat exchangers, fermentation tanks and pipes. Categorical product examples include quaternary ammonium compounds, polymeric materials with antimicrobial pendant groups, antimicrobial peptides, hop acids, vitamin C, and formaldehyde-based products. Enzymatic and engineered biological antibacterial products are also available, such as lactoferrins, lysozyme, biofilm-inhibiting enzymes and bacteriophages.

There is also interest in use of combinations of oxidizing and non-oxidizing products that work synergistically together to provide better bactericidal performance during fermentation.

Sources of bacteria in fermentation processes are many. Often the primary source is in the fermentable feedstock itself and the surrounding environment. Fermentation is typically conducted in a pH range of about 4.5 to 6, which helps to inhibit bacteria growth. However, buildup of biofilms in heat exchanger surfaces, fermentation tanks and pipes are significant sources of contamination in process equipment. Pre-treatment of fermentation feedstocks with appropriate bactericide products can inhibit spoilage and improve enzymatic hydrolysis and fermentation yields. Chemical cleaning and sanitization with oxidizing biocides can be effective for maintaining clean process equipment.

Reactive oxygen species (ROS) exist in natural cellular processes for a variety of reasons. ROS are generated during normal cellular metabolism (e.g., mitochondrial respiratory chain and hydrogen peroxide-generating reactions catalyzed by oxidases). They can also originate from the presence of pro-oxidants (e.g., hydrogen peroxide, menadione, paraquat), by increases in oxygen pressure, or by exposure to ionizing radiations. These ROS include superoxide ($O_2^{\cdot-}$), hydrogen peroxide ($H_2O_2$), hydroxyl radical ($\cdot OH$), and singlet oxygen ($^1O_2$).

ROS may be used as regulated triggers in cell death mechanisms (e.g., apoptosis) or their production increased as defensive responses to cellular threats (e.g., pathogens). The most widely studied ROS in cellular processes involving yeasts, molds and fungus are superoxide and hydrogen peroxide while singlet oxygen can play a role as an antibacterial or antimicrobial agent in plants and animals.

Cells possess both enzymatic and non-enzymatic defense systems to protect their cellular constituents and maintain cellular redox state. ROS can cause oxidative or reductive alterations and damage to cellular constituents such as cell membranes, proteins, nucleic acids and many other components.

Glutathione is one of the most abundant non-enzymatic redox scavenging molecules in cells, including yeast. Glutathione (GSH) is a tripeptide γ-L-glutamyl-L-cystinylglycine, which acts as a radical scavenger with the redox active sulphydryl group reacting with oxidants to produce reduced glutathione (GSSG), a disulfide oligomer.

Under conditions of oxidative stress GSSG levels are increased while altering GSH levels. Researchers have observed that exposure of exponentially growing yeast cells to oxidants for short periods of time does not lead to marked alterations in the levels of total GSH. This result is consistent with the practice of using short-term applications of oxidizing biocides during fermentation processes to selectively control or reduce undesirable bacteria populations while leaving desirable yeast relatively unharmed.

There is a need for highly effective and fast acting oxidizing biocides that are safer to use, have lower environmental impacts and contribute to pollution prevention efforts. Water-based alkyl peroxide salt solutions that efficiently produce reactive oxygen species (ROS) are a class of highly active oxidants that provide multiple biocidal species, have low volatility, degrade to benign residuals, can be produced from stable feedstocks under mild conditions, and reduce or eliminate several harmful disinfection and oxidation byproducts.

It is desirable to find an efficient and cost-effective method of microbial control in fermentation process systems.

SUMMARY

In some embodiments, a method provides for microbial control by reducing the microbial load in fermentation processes using oxidant chemistry. The chemistry provides rapid reduction of bacteria populations in a fermentation process, including a grist or mash, without significant impact on the yeast population or activity. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate oxidant solution may provide enhanced separation of microbes from contaminated water. In some embodiments, the peracetate oxidant solution kills the microbial population in the contaminated water. In some embodiments, the microbes are removed from the contaminated water. In some embodiments, the peracetate solution reduces the biofilms and microbial corrosion.

In some embodiments, a method provides for microbial control and reduction of oxidation byproducts in a fermentation process using highly active peracetate oxidant solutions.

In some embodiments, the contaminated water comprises impurities, and wherein separating the microbes and water phase comprises separating the microbe and water phase into at least microbes, impurities and water.

In some embodiments, the amount of peracetate oxidant solution used is dependent on the severity of contamination, the degree of microbial control desired and residual oxidant solution necessary for effective microbial control.

In some embodiments, the fermentation process stream can be sequentially dosed with peracetate oxidant solution until the degree of microbial control desired is reached and the sequential dosing has a synergistic effect on microbial control. The reducing of the microbial load prevents bacteria in the process water from becoming anaerobic and prevents the formation of sulfides, ammonia, volatile organic acids which result in reduced release of volatile materials and odor control.

In some embodiments, a method is provided for the ability to combine the use of peracetate oxidant solution and an alternative oxidant for improved antimicrobial treatment of water. In some embodiments, the alternative oxidant is selected from the group consisting of chlorine bleach, hypochlorous acid, hypobromous acid, stabilized bromine, iodine and chlorine dioxide.

In some embodiments a method is provided for the ability to combine the use of peracetate oxidant solution and an alternative non-oxidizing biocide for improved antimicrobial treatment of water. In some embodiments, the alternative non-oxidizing biocide is selected from the group consisting of aldehydes and a quaternary ammonium salt.

In some embodiments, a method is provided for reducing the microbial load in contaminated water previously treated with an alternative oxidant by treating with a peracetate oxidant solution for improved microbial control of water.

In some embodiments, heating or thermal activation of peracetate oxidant solutions to a temperature between about 38° C. to about 95° C. accelerates the formation of ROS daughter products as shown by greatly enhanced bleaching and biocidal activity with increasing temperature. Thermal activation that accelerates ROS production rate is useful for microbial control in heated environments and hot chemical sanitizing processes.

In some embodiments, a method is provided for reducing the microbial load in a slurry comprising containing a population of microbes with a peracetate oxidant solution; and mixing said slurry with the peracetate oxidant solution.

In some embodiments, the peracetate oxidant solutions are particularly suited for use in water with high salinity, alkalinity and contamination as they rely on reactive oxygen species whose performance is little impacted or enhanced by such conditions, in contrast to common Fenton and advanced oxidation processes that produce hydroxyl radical or ozonides as the primary ROS. The peracetate oxidant does not form bromate in bromide-containing water under typical treatment conditions, which is a benefit for treated water discharge. In some embodiments, the peracetate oxidant has a very low organic halide formation potential in fermentation processes compared to chlorine and chlorine dioxide.

In some embodiments, the peracetate oxidant solution is generated at, or near, the point of use as an aqueous solution due to its high activity and relatively short half-life of minutes to hours depending on concentration and use conditions. The oxidant is active long enough to serve as a biocide before it attenuates leaving benign and readily degradable residuals including oxygen, sodium acetate and glycerol.

In some embodiments, the peracetate oxidant solution has low volatility because it is a solid in its native form and it forms a mildly alkaline solution. The peracetate oxidant solution can be significantly less corrosive in solution and the vapor phase than many common oxidants over a range of concentrations and temperatures. Low volatility is also a benefit for using peracetate oxidant solutions in warm environments such as hot chemical sanitizing, cooling tower water loops, pulp bleaching and paper making.

In some embodiments, the contaminated water contains a population of microbes which may include slime forming bacteria, anaerobic sulfate reducing bacteria, anaerobic nitrate reducing bacteria, aerobic acid producing bacteria, iron related bacteria, fungi, molds, yeast, algae and microbes resistant to standard biocides.

Some example embodiment combinations of this disclosure are as follows:

1. A method to control bacteria during fermentation processing in a yeast fermentation system to produce an alcohol product, the yeast fermentation system including a fermentation operation with at least one fermenter containing an active fermentation mixture with yeast producing the alcohol by fermentation, the method comprising oxidative treatment of a process liquid of the fermentation system for bacterial control, the oxidative treatment comprising:

introducing a peracetate oxidant solution into a process liquid in the fermentation system, wherein at the time of the introducing the process liquid is in the fermenter in or to become a part of the active fermentation mixture or the process liquid is in a fluid communication path through which the process liquid is added to or becomes a part of the active fermentation mixture after the introducing, and wherein prior to introduction into the process liquid during the introducing the peracetate oxidant solution comprises the following properties:

a pH in a range of from pH 10 to pH 12; and
   either no hydrogen peroxide or hydrogen peroxide at a molar ratio of peracetate to hydrogen peroxide of greater than 16:1; and after the introducing, generating reactive oxygen species in the process liquid for bacterial control in the process liquid as a consequence of the peracetate oxidant solution introduced into the process liquid.

2. The method of example combination 1, comprising preparing the peracetate oxidant solution with the properties and performing the introducing within 30 minutes after the preparing the peracetate oxidant solution with the properties.

3. The method of example combination 2, wherein the preparing the peracetate oxidant solution comprises mixing alkaline hydrogen peroxide solution with an acyl donor at a molar excess of acyl donor reactive groups to hydrogen peroxide with a molar ratio of acyl donor reactive groups to hydrogen peroxide of at least 1.25:1.

4. The method of example combination 3, wherein the molar ratio of acyl donor reactive groups to hydrogen peroxide is in a range from 1.25:1 to 4:1.

5. The method of any one of example combinations 2-4, comprising after the preparing the peracetate oxidant solution with the properties, diluting the peracetate oxidant solution prior to the introducing.

6. The method of example combination 4, wherein the molar ratio of acyl donor reactive groups to hydrogen peroxide is in a range of from 1.5:1 to 2.5:1.

7. The method of any one of example combinations 1-6, wherein the process liquid has a first oxidation-reduction potential (ORP) value versus standard hydrogen electrode (SHE) prior to the introducing and the oxidative treatment comprises raising the ORP of the process liquid after the introducing to a second ORP value that is at least 100 millivolts larger than the first ORP value.

8. The method of example combination 7, wherein the second ORP value is at least 200 millivolts larger than the first ORP value.

9. The method of either one of example combination 7 or example combination 8, comprising performing multiple sequential occurrences of the oxidative treatment of the process liquid, and wherein:

between said sequential occurrences of the oxidative treatment, the ORP of the process liquid is reduced from the second ORP value to a third ORP value that is at least 100 millivolts smaller than the second ORP value.

10. The method of any one of example combinations 1-9, wherein the process liquid is in the active fermentation mixture in the fermenter.

11. The method of any one of example combinations 1-9, wherein the process liquid is in a yeast propagation mixture under aerobic conditions.

12. The method of any one of example combinations 1-9, wherein the process liquid is in a feedstock stream comprising a feedstock for the fermentation processing in the fermentation system.

13. The method of example combination 12, wherein the feedstock comprises a member selected from the group consisting of cellulosic feedstock, starch feedstock and sugar feedstock.

14. The method of either one of example combination 12 or example combination 13, wherein the feedstock stream is a pulp slurry comprising feedstock solids slurried with the process liquid.

15. The method of example combination 14, wherein the pulp slurry is at a pH of at least pH 9.

16. The method of either one of example combination 14 or example combination 15, wherein the fermentation system comprises a hydrolysis operation upstream of the fermentation operation;

the feedstock solids comprise cellulosic material selected from the group consisting of cellulose, hemicellulose and combinations thereof; and the feedstock stream is a feed stream to the hydrolysis operation of the fermentation system to convert the cellulosic material to sugars in the hydrolysis operation for processing in the fermentation operation.

17. The method of either one of example combination 12 or example combination 13, wherein the fermentation system comprises a hydrolysis operation upstream of the fermentation operation; and the feedstock stream comprises starch and is a feed stream to the hydrolysis operation to convert the starch to sugars for subsequent processing in the fermentation operation.

18. The method of any one of example combinations 1-9, wherein the process liquid is in a water stream to provide make-up water to the fermentation processing.

19. The method of example combination 18, wherein fermentation system comprises a distillation operation to distill product liquid comprising alcohol recovered from the fermentation operation, and the water stream comprises recycle water from the distillation operation.

20. The method of any one of example combinations 1-9, wherein the process liquid is in a mixture containing yeast prior to introduction into the fermenter.
21. The method of any one of example combinations 1-20, wherein the alcohol is ethanol.
22. The method of any one of example combinations 1-21, wherein the process liquid prior to the introducing has a pH of at least pH 4.5.
23. The method of any one of example combinations 1-21, wherein the process liquid prior to the introducing has a pH in a range of from pH 4.5 to pH 6.
24. The method of any one of example combinations 1-23, wherein the properties comprise a concentration of peracetate, measured as peracetic acid, in a range of from 0.2 weight percent to 5 weight percent.
25. The method of any one of example combinations 1-24, wherein the introducing comprises dosing the peracetate oxidant solution into the process liquid to provide a concentration of peracetate, measured as peracetic acid, in the process liquid in a range of from 20 ppm by weight to 100 ppm by weight, preferably not more than 80 ppm and more preferably not more than 60 ppm.
26. The method of any one of example combinations 1-25, wherein the process liquid has a temperature in a temperature range of from 20° C. to 50° C. during at least a portion of the generating.
27. The method of example combination 26, wherein a temperature of the process liquid is at a first temperature below the temperature range prior to the introducing and the oxidative treatment comprises raising the temperature of the process liquid to a second temperature in the temperature range during or following the introducing.
28. The method of example combination 26, wherein the temperature of the process liquid is within the temperature range prior to the introducing.
29. The method of any one of example combinations 1-28, wherein the properties include a molar ratio of peracetate anions to peracid in a range of from 60:1 to 6000:1.
30. The method of any one of example combinations 1-16, wherein the properties include either no hydrogen peroxide or hydrogen peroxide at a molar ratio of peracetate to hydrogen peroxide greater than 25:1.
31. The method of any one of example combinations 1-30, wherein the reactive oxygen species comprise singlet oxygen and superoxide.
32. The method of any one of example combinations 1-31, comprising monitoring the ORP of the process liquid after the introducing and adjusting a rate of introduction of the peracetate oxidant solution into the process liquid during the introducing based on the monitored ORP.
33. The method of any one of example combinations 1-32, wherein the introducing comprises injecting the peracetate oxidant into a flowing stream comprising the process liquid.
34. A method for preparing a yeast culture for use in yeast fermentation processing to produce an alcohol product, the method comprising:
culturing yeast in a culture mixture including a liquid-containing culture medium to multiply the yeast and prepare an active yeast culture for introduction into a fermenter to produce the alcohol product;
introducing a peracetate oxidant solution into the liquid of the culture mixture for bacterial control, wherein prior to introduction into liquid of the culture mixture during the introducing, the peracetate oxidant solution comprises the following properties:
a pH in a range of from pH 10 to pH 12; and
either no hydrogen peroxide or hydrogen peroxide at a molar ratio of peracetate to hydrogen peroxide of greater than 16:1.
35. The method of example combination 34, wherein at the time of the introducing, the culture mixture is in a yeast propagation phase under aerobic conditions.
36. The method of either one of example combination 34 or example combination 35, wherein the culture mixture is at a pH in a range of pH 4.5 to pH 6 during the introducing.
37. The method of any one of example combinations 34-36, wherein the temperature of the culture mixture is in a range of from 20° C. to 50° C. during the introducing.
38. The method of any one of example combinations 34-37, wherein the introducing comprises adding the peracetate oxidant solution into the culture mixture to provide a concentration of peracetate, measured as peracetate acid, in a range of from 20 ppm to 100 ppm, preferably no more than 80 ppm and more preferably no more than 60 ppm.
39. The method of example combination 38, comprising after the introducing, adding the yeast culture to a fermenter and conducting fermentation in the fermenter to produce an alcohol.
40. A yeast fermentation system for fermentation processing of biomass feedstock to prepare an alcohol product and with chemical oxidant bacterial control, the system comprising:
an alcohol production system with fluidly-connected operations to prepare the alcohol product from biomass feedstock, the alcohol production system comprising:
a feedstock processing operation to process a biomass feedstock to prepare a sugar-containing feed for subjecting to fermentation;
a fermentation operation in fluid communication with the feedstock processing operation to receive and process the sugar-containing feed to prepare a raw fermentation product comprising the alcohol, the fermentation operation comprising at least one fermenter for fermentation of sugar in the sugar-containing feed to produce the alcohol; and
a product recovery operation in fluid communication with the fermentation operation to receive and process the raw fermentation product to prepare a separated alcohol product;
wherein the sugar-containing feed, the active fermentation mixture and the raw fermentation product is each in a form of a flowable composition comprised of a majority by mass of aqueous process liquid;
a bacterial control oxidant supply system in fluid communication with the alcohol production system to supply a peracetate oxidant solution for delivery to the alcohol production system for introduction into a said process liquid at one or more locations in the alcohol production system, each said location being an oxidant introduction location in the fermenter to introduce the peracetate oxidant solution into or to become a part of the active fermentation mixture in the fermenter or an oxidant introduction location from which the process liquid moves through a fluid communication path of the alcohol production system to be added to or to become a part of the active fermentation mixture in the fermenter;

the peracetate oxidant solution as supplied from the bacterial control oxidant supply system comprises the following properties:

a pH in a range of from pH 10 to pH 12; and
either no hydrogen peroxide or hydrogen peroxide at a molar ratio of peracetate to hydrogen peroxide of greater than 16:1;
wherein the peracetate oxidant solution causes generation of reactive oxygen species in the process liquid for bacterial control.

41. The yeast fermentation system of example combination 40, comprising a said location in the fermentation operation to introduce the peracetate oxidant solution into the active fermentation mixture.
42. The yeast fermentation system of either one of example combination 40 or example combination 41, wherein:

the alcohol production system comprises a water supply operation to provide water of the aqueous process liquid; and the alcohol production system comprises a said location in the water supply operation to introduce the peracetate oxidant solution into make-up water for operation of the alcohol production system.

43. The yeast fermentation system of example combination 42, wherein the said location in the water supply operation introduces the peracetate oxidant solution into recycle water from the product recovery operation for reuse in the alcohol production system.
44. The yeast fermentation system of any one of example combinations 40-43, comprising a said location in the feedstock preparation operation to introduce the peracetate oxidant solution into a process composition comprising the aqueous process liquid and a biomass feedstock component selected from the group consisting of a sugar, a starch, cellulose and combinations thereof.
45. The yeast fermentation system of any one of example combinations 40-44, wherein:

the alcohol production system comprises a yeast supply operation in fluid communication with the fermentation operation to prepare and provide a yeast culture mixture to the fermentation operation; and the alcohol production system comprises a said location in the yeast supply operation to introduce the peracetate oxidant solution into the yeast culture mixture or liquid that becomes part of the starter culture.

46. The yeast fermentation system of any one of example combinations 40-45, wherein the bacterial control oxidant supply system comprises precursors for combination to prepare the peracetate oxidant solution.
47. The yeast fermentation system of example combination 46, wherein the precursors comprise an alkaline hydrogen peroxide solution and an acyl donor.
48. The yeast fermentation system of example combination 46, wherein the precursors comprise hydrogen peroxide solution, alkali and an acyl donor.

BRIEF DESCRIPTION OF THE DRAWINGS

Advantages of the present invention may become apparent to those skilled in the art with the benefit of the following detailed description of the preferred embodiments and upon reference to the accompanying drawings.

DETAILED DESCRIPTION

Figure 1:
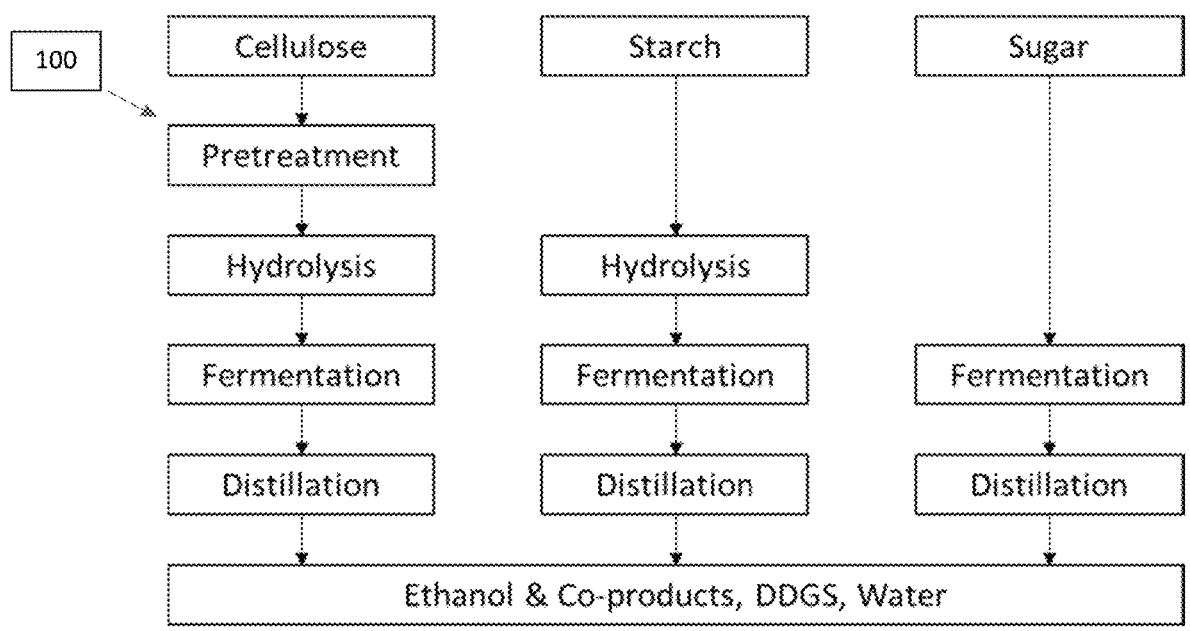
FIG. 1 is a simplified schematic diagram of an embodiment of an ethanol production process from different fermentation feedstocks.

Unless defined otherwise, all technical and scientific terms used herein have the same meaning as commonly understood by one of ordinary skill in the art.

The term "fermentation feedstock" as used herein generally refers to biomass feedstock such as sugar cane, sugar beets, sorghum, wheat, barley, corn, cassava, sweet potato, molasses, lactate and cellulosic materials including corn stover, switchgrass, wheat straw, reed, bagasse, wood, paper.

The term "grist" as used herein refers to grain that has been separated from its chaff in preparation for grinding, The term "reactive oxygen species" as used herein generally refers to a species such as may include singlet oxygen ($^1O_2$), superoxide radical ($O_2^{\cdot-}$), hydroperoxyl radical (HOO$^{\cdot}$), hydroxyl radical (HO$^{\cdot}$), acyloxy radical (RC(O)—O$^{\cdot}$), and other activated or modified forms of ozone (e.g., ozonides and hydrogen trioxide). Each of these ROS has its own oxidation potential, reactivity/compatibility profile, compatibility/selectivity and half-life.

The term "reactive species oxidant" as used herein generally refers to oxidant formulations containing or capable of evolving at least one reactive oxygen species and can evolve at least one reactive carbon species. Such reactive species enhance the oxidative or reductive performance of the precursor formulation constituents.

The term "microbes" as used herein generally refers to aerobic and anaerobic bacteria (slime formers, acid producers, metal depositors, nitrobacteria, sulfate reducers, nitrate reducers), fungi, algae, molds, and yeast.

The current invention describes methods of controlling bacteria in fermentation processes using an oxidation chemistry that delivers reactive oxygen species. This invention describes methods of increasing efficiency in fermentation processes by using an oxidation chemistry that delivers reactive oxygen species.

An ideal chemistry for bacteria control in a fermentation process should meet several performance criteria listed here. The chemistry should provide rapid reduction of bacteria populations in a fermentation process, including a grist or mash, without significant impact on the yeast population or activity. The chemistry should be consumed relatively quickly and leave behind non-toxic residuals which are compatible with processing methods and products. The chemistry should not have a significant impact on the pH or other conditions of a fermentation process. The chemistry should be highly active over a relatively wide pH range. The chemistry should have a low corrosion profile on process equipment. The chemistry should work efficiently in the presence of high organic solids loading as well as high dissolved solids including salinity. The chemistry should avoid producing halogenated organic byproducts. The chemistry should be non-volatile so that it is not lost to vapor in warm and turbulent environments. The chemistry should be compatible with the primary fermentation products, such as ethanol. Byproducts or residuals of the chemistry should be easily separated from the ethanol product during distillation.

There is a need for highly effective and fast acting oxidizing biocides that are inherently safer to use, have lower environmental impacts and contribute to pollution prevention efforts. Water-based alkyl peroxide salt solutions that efficiently produce reactive oxygen species (ROS) are a class of highly active oxidants that provide multiple biocidal species, can be produced from stable feedstocks under mild conditions, and meet all the above performance criteria. Biocides used for microbial control need to be effective and efficient at neutral and alkaline pH. They also need to be effective at elevated levels of suspended solids and dissolved solids. Oxidizing biocides are a fast-acting line of defense and represent a significant expense in operations. Oxidizing biocides should be very active and have a limited lifetime with no reactive residuals so that they do not interfere with non-oxidizing biocide chemicals used to provide longer-term biostatic conditions.

In some embodiments, oxidation chemistry may be used for microbial control of fermentation processes. The oxidation chemistry used may have minimal impacts on pH and scaling potential of fluids. A relatively short-lived active oxidant may be a benefit for avoiding negative impacts on pulp quality, fermentation feedstock quality, food product quality and for minimizing oxidant corrosivity and environmental impacts. Selectivity of the oxidation chemistry towards different materials is also desirable for efficiency of oxidant use, compatibility with a variety of materials and avoidance of unnecessary or undesirable side reactions. Oxidant solutions that generate a variety of reactive oxygen species (ROS) in their treatment environments may be good candidates for achieving some or all of these attributes.

ROS may be generated in-situ by several chemical methods including the Fenton catalytic cycle with hydrogen peroxide and iron catalysts (produces hydroxyl and superoxide radicals), combining ozone with hydrogen peroxide (produces ozonides and oxygen-based radicals), and combining hypochlorite with hydrogen peroxide (produces singlet oxygen). Other methods of generating ROS may include photochemical approaches, which are generally very dilute in ROS and are not practical for large volume treatment systems or for highly scaling fluids or fluids with high turbidity.

Some ROS (e.g., hydroxyl radical and ozonides) are too short lived and too reactive to be practical in highly contaminated or hydrocarbon environments. Salt and carbonate may rapidly quench the hydroxyl radical. Ozone and stronger oxidants, like hydroxyl radical, oxidize salts to form toxic chlorate and bromate byproducts. Chlorine-containing oxidant formulations are typically more corrosive than peroxides, are less efficient for $H_2S$ oxidation and rapidly chlorinate unsaturated hydrocarbons.

In some embodiments, a method provides for microbial control fermentation processes. The methods may include providing a preferred ROS-producing oxidant formulation, peracetate oxidant solution.

In some embodiments, one preferred ROS-producing oxidant formulation is a peracetate solution. The peracetate solution may include generating an alkaline hydrogen peroxide solution from the combination of an alkali and a hydrogen peroxide concentrate, mixing the alkaline hydrogen peroxide solution with an acyl donor such that a peracetate solution concentrate is formed. In some embodiments, the peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1.

In embodiments, the peracetate solution efficiently generates singlet oxygen in combination with superoxide, hydroperoxyl radical and other reactive species, which together provide an oxidative-reductive potential (ORP) level significantly greater than dissolved oxygen in a water mixture at a given pH. In embodiments, biocide dosing in a process stream may be monitored and controlled by measuring the oxidation-reduction potential of a fermentation mixture, grist, slurry or water in which the peracetate solution is applied. In some embodiments, the ORP is about 100 to 300 mV greater than dissolved oxygen. In some embodiments, the ORP is about 300 to 500 mV greater than dissolved oxygen. In other embodiments, the ORP is about 600 mV up to about 1100 mV versus standard hydrogen electrode.

The oxidation-reduction potential (ORP) can be correlated with a level of biocidal control at a given pH and may be correlated with the concentration of an active biocide present. Various forms of chlorine, bromine, chlorine dioxide and sometimes ozone can provide a strong ORP response when used at low concentrations at slightly acidic to moderately alkaline pH. For example, the ORP of chlorine bleach or chlorine dioxide at a 1-2 ppm concentration in relatively clean fresh water at pH 7 can exceed 700 mV vs standard hydrogen electrode (ORP greater than 650 mV typically provides effective bacteria control). In contrast, peracetic acid (PAA), hydrogen peroxide and non-oxidizing biocides do not provide meaningful or reliable ORP responses above a dissolved oxygen background, which is about 420-520 mV vs standard hydrogen electrode at pH 7 in fresh water.

In some embodiments, the peracetate oxidant solution is generated at, or near, the point of use as an aqueous solution due to its high activity and relatively short half-life of minutes to hours depending on concentration and use conditions. The peracetate oxidant solution generates reactive oxygen species at the expense of the peracetate concentration. The oxidant is active long enough to serve as a biocide before it naturally attenuates leaving benign and readily degradable residuals including oxygen, sodium acetate and glycerol, materials that are generally regarded as safe (GRAS) as food additives and are easily separated from the ethanol product (remain in the stillage and can be substantially drained off DDGS).

In some embodiments, the peracetate oxidant solution has low volatility because it is a solid in its native form and it forms a mildly alkaline solution. The peracetate oxidant solution can be significantly less corrosive in solution and the vapor phase than many common oxidants over a range of concentrations and temperatures. Low volatility is a benefit for using peracetate oxidant solution in warm environments because it remains in solution where it is needed.

In some embodiments, the contaminated fermentation process or feedstock contains a population of microbes, which may include slime forming bacteria, sulfate reducing bacteria, nitrate reducing bacteria, acid producing bacteria, fungi, molds, yeast, and algae. The present invention utilizes a combination of ROS delivered in bulk quantities and applied at lower concentrations that are tailored to kill bacteria, but not overwhelm cellular defense mechanisms of yeast against ROS and oxidative alterations.

It is known that exposure of exponentially growing yeast cells to moderate concentrations of oxidants, including chlorine dioxide and peracetic acid, for short periods of time does not lead to marked alterations in yeast activity or the onset of oxidative stress. In contrast, the inventors have observed that bacteria in the exponential growth phase are most readily killed using the ROS generated by the peracetate formulation. The inventors have also observed that using the ROS generated by the peracetate formulation can increase the efficacy performance of non-oxidizing biocides applied shortly thereafter.

In an embodiment, one or more reactive oxygen species produced by, and in combination with, the parent oxidant formulation provide microbial control in a fermentation process or environment including grist. Reactive oxygen species include singlet oxygen, superoxide, hydroperoxyl radical, and combinations or complexes thereof.

FIG. 1 illustrates the general process steps of an ethanol production process, illustrated for an example ethanol production system 100, using different types of feedstocks including cellulose, starch and sugar sources. Cellulosic feedstocks, such as corn stover and wood, require the most processing to break down fiber structures. Cellulosic materials may be mechanically and chemically pulped in the pretreatment step. The cellulose and hemicellulose is then hydrolyzed by acid and/or enzyme treatments (also known as liquefaction) to shorter polysaccharide chains that are converted by Amylase enzymes to fermentable sugars (e.g., hexose, pentose, xylose, glucose). The fermentation step is typically conducted with yeast, enzymes, yeast vitamins, a carbon source (urea), antifouling agent and optionally a bactericide. After fermentation the ethanol is recovered by distillation. The stillage is dewatered to recover the remaining solids and the water may be recycled back into the production process.

Starch feedstocks, such as corn and grains, require less processing than cellulose. These feedstocks are milled to a flour and treated with Amylase in the hydrolysis step to convert starches to sugars. Sugar feedstocks, such as sugar cane and sorghum, can be milled and extracted directly for fermentation and are the least expensive to process. Solids recovered from the stillage, known as distillers dried grains with solubles (DDGS), are converted to animal feed starch and sugar sources are recovered and used in animal feed.

The peracetate oxidant may be used in a variety of places in the above ethanol production processes.

In an embodiment, a method of pretreating a cellulose feedstock for ethanol production uses the peracetate oxidant solution for delignification, which may improve hydrolysis efficiency while avoiding the production of halogenated organic byproducts. Methods of delignification with the peracetate oxidant solution are described in U.S. patent Ser. No. 15/371,872.

The reactive oxygen species (ROS) that may be generated as a consequence of use of the peracetate oxidant solution disrupt lignin structures, expand plant fiber structures and increase accessibility to cellulose in those fiber structures for more efficient hydrolysis and sugar yield. The ROS have much less impact on hemicellulose and kappa number reduction than other oxidants used for delignification including chlorine, chlorine dioxide, alkaline hydrogen peroxide and ozone.

In an embodiment, a method of treating a fermentation feedstock with the peracetate oxidant solution to control microbes and odors and disinfect a feedstock to reduce or prevent microbial contamination of an ethanol production process.

In an embodiment, a method of reducing bacterial growth in a fermentation process stream, wherein the method includes introducing a peracetate oxidant solution into the process at an injection point, mixing the peracetate with the process stream containing a population of bacteria, generating a reactive oxygen species solution in the stream and reducing the bacteria growth in the process stream.

In an embodiment, a method of treating a fermenter with the peracetate oxidant solution before, during or after fermentation to reduce or control a bacteria population contaminating the fermentation stage.

In an embodiment, a method of treating water recovered from a fermentation process with the peracetate oxidant solution, wherein the method of treatment reduces or eliminates microbe from the water and may be used to enable removal of impurities from the recovered water, which may include suspended solids, biomass, yeast, transition metals, oils, rosin, and lignin.

ROS-generating peracetate oxidant solutions may contain no hydrogen peroxide, and are produced on site and on demand at alkaline pH. The peracetate oxidant solution produces multiple ROS by itself and when placed into contaminated environments. In some embodiments, the ROS most important in peracetate oxidant solutions include singlet oxygen, superoxide radical, hydroperoxyl radical, acetyloxy radical and potentially other radical fragments. When a combination of these ROS are generated together in peracetate oxidant solutions they produce an oxidative-reductive potential (ORP) response in water that may exceed 900 mV (vs standard hydrogen electrode) around pH 7. These solutions may be more convenient and effective to use than other approaches. The dominant ROS may be selectively reactive such that they are effective in a variety of environments.

In some embodiments, a method may include making a reactive species formulation. The method may include providing an alkaline hydrogen peroxide solution. The method may include contacting the alkaline hydrogen peroxide solution with an acyl donor. A peracid concentrate may be produced by the contacting of the alkaline hydrogen peroxide with the acyl donor. The peracid concentrate may have a molar ratio of acyl donor reactive groups to hydrogen peroxide ranging from about 1.25:1 to about 4:1. The method may include maintaining the peracid concentrate pH value in a range from about pH 10 to about pH 12.

In some embodiments, a method of reducing the microbial load (bacterial growth) in a fermentation process may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water.

In some embodiments, a method reducing the microbial load in contaminated water further comprises separating the population of microbes from the contaminated water may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water. In some embodiments, the method may include separating, after the contacting of the peracid composition and the mixing of contaminated water containing a population of microbes, into one of microbes and one of water.

In an embodiment, the rate of ROS generation by the peracetate formulation is directly proportional to the rate of peracetate concentration decline. In some embodiments, the rate of ROS generation is thermally activated to accelerate delignification. Measurement of peracetate concentration over time was conducted in clean tap water and in 5% consistency hardwood pulp at 70° C., which is a common temperature for pulp delignification and bleaching processes in a paper mill.

In some embodiments, a method reducing the microbial load in contaminated water further comprises a method of separating the population of microbes and contaminated water containing impurities may include: providing a contaminated water containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the contaminated water. In some embodiments, the method may include mixing, after the contacting of the peracid composition and the contaminated water. In some embodiments, the method may include separating, after the contacting of the peracid composition and the mixing of contaminated water containing a population of microbes, into one of microbes, impurities and one of water.

In some embodiments, a method reducing the microbial load in contaminated water further comprises a method of heating contaminated water in a range from about 38° C. to about 95° C. prior to or following contacting with a peracid composition. Thermal activation that accelerates ROS production rate is useful for microbial control in heated environments and hot chemical sanitizing processes. Peracetate oxidant is more effective for microbial control in alkaline water than chlorine bleach and peracetic acid. Peracetate oxidant solution can be thermally activated to enhance its production of ROS and biocidal activity. Thermal activation is useful for microbial control in warm and hot water environments.

In some embodiments, a method of reducing the microbial load in a slurry may include: providing a slurry containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the slurry. In some embodiments, the method may include mixing, after the contacting of the peracid composition and the slurry. For example, after a starch feedstock has been crushed pulverized or ground and hydrated with water to its mash consistency (e.g., a slurry containing about 30% solids for the hydrolysis step) the slurry may be treated with the peracetate oxidant solution to reduce bacteria contamination. The peracetate oxidant solution may be added during or after heating of the slurry to elevated temperatures used for enzymatic hydrolysis (e.g., 85° C. mash temperature), but preferably at a pH above about pH 5.5. Above about 50° C. the oxidant is consumed within 10 minutes, after which Amylase, nutrients and other enzymes may be added to promote hydrolysis and fermentation.

In some embodiments a method is provided for the ability to combine the use of peracetate oxidant solution and an alternative non-oxidizing biocide for improved antimicrobial treatment of water. In some embodiments, the alternative non-oxidizing biocide is selected from the group consisting of aldehydes and a quaternary ammonium salt.

In some embodiments, the peracetate oxidant solution is shown to reduce toxic organic halide formation (e.g., chlorinated phenols, dioxins, haloacetic acids) during the fermentation process. For example, utilizing peracetate oxidant produces about ten times less total organic halides (TOX) than chlorine dioxide and about 2.5 times less TOX than peracetic acid.

The ability to mitigate microbes that have developed resistance to biocides is a growing challenge. Changing the biocide type periodically is one method used to mitigate microbes that have developed resistance to a particular biocide. This approach is often used in managing microbial populations in cooling tower water and other industrial water applications. However, resistance to multiple forms of chlorine and bromine has created problems with virulent pathogens that are increasingly resistant to antibiotics.

The peracetate oxidant solution provides several different oxidant species in a single solution including the peracetate parent oxidant and several daughter products formed in-situ including singlet oxygen, hydroperoxyl radical, superoxide radical and combined forms that impart high oxidative-reductive potentials (ORP) that are desirable for and correlated with effective microbial control. The combination of multiple oxidant species along with a high ORP can help mitigate resistance of microbes to disinfectants.

The presence of ROS or other reactive species in the formulations herein may in some cases be directly detected and it may be possible to determine the concentrations of certain reactive species (e.g., using spectroscopic methods). However, in some embodiments, in formulations herein the presence of reactive species may only be indirectly demonstrated by measurement of changing properties of the formulation (e.g., ORP measurements or pH change), by changes in concentration of precursors (e.g., rate of peroxyacetic acid concentration decline) or by changes in reactivity of the formulation (e.g., the rate of oxidation of dyes (bleaching rate)) or the rate or occurrence of oxidation of certain species (e.g., polysaccharide breakdown).

The oxidative reductive potential (ORP), also referred to herein as oxidation-reduction potential, is a measure of how oxidizing or reducing a solution is relative to a standard reference potential measured in volts. Standard reference potentials are measured relative to the hydrogen/hydrogen ion reduction-oxidation potential of 0.000 V at unit activity for the standard hydrogen electrode (SHE). Generally, solutions with potentials greater than 0 V vs SHE are considered oxidizing (electron accepting) while solutions with potentials less than 0 V vs SHE are considered reducing (electron donating). The measured ORP of water is influenced by its pH or hydrogen ion activity. As the hydrogen ion activity (e.g., concentration, temperature) increases, the ORP of water increases to more positive values. ORP is also influenced by the presence of reducing or oxidizing agents relative to their standard reduction-oxidation potentials and solution activities. All references herein to oxidation-reduction potential (ORP) are relative to a standard hydrogen electrode (SHE).

Standard oxidation potentials are often cited to compare the oxidative strength of oxidants. The standard potential is a thermodynamic value which is always greater than the measured ORP in solution for a given oxidant. This difference is caused in part by kinetic factors, such as the over potential or activation barrier of electron transfer at an electrode surface and the solution activity of the oxidant, which is proportional to the concentration. As a result, the standard potential is not a reliable measure of the chemical reactivity or antimicrobial activity of an oxidant regarding its reaction rate or reaction mechanism with a substrate. In contrast, a solution's ORP can be correlated with the level of microbial control for a given oxidant by measuring the reduction in microbial content achieved at that ORP in a given environment.

For example, according to the standard potentials hydrogen peroxide is a stronger oxidant than hypochlorous acid. However, the ORP of hypochlorous acid (29 mM) at pH 7 is over 1.1 V (vs SHE) while the ORP of hydrogen peroxide (29 mM) at pH 7 is about 0.5 V (vs SHE) indicating that hypochlorous acid is the stronger oxidant and biocide. Free radicals of chlorine are strong electron acceptors and also rapidly attack and substitute unsaturated and aromatic hydrocarbons, amines, thiols, aldehydes, ketones, and biological materials such as DNA and proteins. Hydrogen peroxide is a strong electron acceptor, but it is not a free radical, is less chemically reactive and exhibits lower antimicrobial activity than chlorine. This difference in chemical reactivity is reflected in the ORP. In practice, chlorine is used as a broad-spectrum biocide in water treatment whereas hydrogen peroxide is not.

ORP is used as a general measure of the antimicrobial strength of a solution containing an oxidizing antimicrobial agent, biocide or disinfectant. ORP may be correlated to relative oxidant concentration for lower oxidant concentrations at constant pH and temperature. This feature is the basis for ORP monitoring systems sometimes used in water treatment and disinfection processes where oxidant dose may be adjusted to maintain a desired ORP and corresponding biocidal activity for a particular oxidant.

Water solutions containing oxidizing biocides which have ORP's of greater than about 650 mV (vs SHE) are generally considered to be suitable for disinfection (Suslow, T. "Oxidation-Reduction Potential (ORP) for Water Disinfection Monitoring, Control, and Documentation" Univ. California Publication 8149 http://anrcatalog.ucdavis.edu which is incorporated by reference as if fully set forth herein) while ORP's above about 800 mV (vs SHE) are suitable for sterilization. Below about 475 mV (vs SHE) there is typically little to no biocidal activity for oxidizing biocides even after long contact times. Known exceptions to these ORP benchmarks include in-situ generation of short-lived reactive oxygen species such as hydroxyl radical, by ultraviolet-activated hydrogen peroxide, or singlet oxygen, by dye-sensitized photo-activation of molecular oxygen. Although the peracetate oxidant solution produces short-lived ROS, the combination of ROS and the parent peracetate oxidant create a metastable complex or a new species which exhibits an elevated solution ORP which can be correlated with effective microbial control.

There are several limitations to ORP measurement as a method for evaluating antimicrobial activity. ORP is normally not sensitive to very short-lived reactive oxygen species such as hydroxyl radicals, singlet oxygen, hydrogen trioxide and hydroperoxide radical in the presence of parent oxidants such as, for example, hydrogen peroxide, peroxyacetic acid, molecular oxygen and ozone. ORP is not sensitive to non-oxidizing biocides and chemical reactivity which impart other mechanisms for disrupting cellular viability. Examples of non-oxidizing chemical biocides include glutaraldehyde, which acts by crosslinking protein structures, and antimicrobial quaternary ammonium compounds, which disrupt cell membranes. ORP is also insensitive to the tolerance of various microorganisms to a given biocide, which affects the concentration and contact time required to inactivate or destroy a specific microorganism. For example, chlorine use in water treatment is not effective against certain spores (e.g., *Cryptosporidium* oocysts) while chlorine dioxide and ozone are.

In some embodiments, the formulations may be used in various applications as oxidants and/or biocides. As described herein, different formulations, as assessed by ORP measurement and dye oxidation rate among other properties, may exhibit enhanced activity as a chemical oxidant or as a disinfectant, antimicrobial or biocide.

Reactive oxygen species formulations may be employed as an antimicrobial agent or oxidizing agent for treatment of water, including without limitation, process streams or waste streams. Reactive oxygen species formulations may be used in water treatment: to cause chemical transformation or degradation of components or contaminants; to promote or enhance flocculation, micro-flocculation, coagulation and subsequent clarification and separation of inorganic and organic materials; to promote or enhance biological treatment processes; to promote or enhance wet peroxide oxidation processes; as a pretreatment, intermediary treatment or post treatment process to other treatment and separation processes.

In water treatment processes, the chlorine-free and bromine-free reactive oxygen species formulations may be used to provide treatment without formation of undesired chlorinated or brominated byproducts. In water treatment processes, the chlorine-free and bromine-free active oxygen species formulations may be used to provide treatment in the absence of chlorine, chlorine dioxide and/or ozone.

For applications of the formulations herein the formulation is contacted with a substrate or environment to be oxidized or treated. Any means of contacting may be employed, that is suitable for retention of the oxidation activity of the formulation and that is suitable for the environment and/or substrate. Formulations are liquid and may be employed in a concentrated form or a diluted form. Formulations may be diluted, if desired, before, during or after initial contact. The concentration of formulations in contact with an environment and/or substrate may be varied during contact.

A given application may employ separate contacting events which may be the same or different and which may employ the same formulation or precursor formulation. A given application may employ contact with more than one formulation or precursor thereof. The environment and/or substrate may, for example, be contacted with an activated liquid formulation containing reactive oxygen species. Alternatively, the environment and/or substrate may be contacted with a liquid precursor formulation that will generate reactive oxygen species on activation and the formulation is activated as or after it comes into contact with the environment or substrate.

For example, the environment or substrate may itself provide for activation, such as providing acidity that affects ROS formation rates and changes in oxidant speciation, fragmentation behavior or reactivity caused by acid-base equilibria. One or more additional steps of activation to form additional reactive species may occur after the contact of the formulation or the precursor formulation with the environment and/or substrate. For example, redox active materials or charged materials including transition metal species, unsaturated organic materials, sulfides and suspended solids can interact with and react with the parent peracetate oxidant to initiate fragmentation of the parent peracetate oxidant leading to the formation of ROS. Thermal activation can also be used to increase the formation rate of ROS, increase the fragmentation rate of the peracetate and increase overall peracetate oxidant solution's antimicrobial activity, bleaching power and reactivity with impurities or substrates. Irradiation of peracetate-containing solutions with ultraviolet light may also be used to promote activation. Contact with the environment or substrate may be controlled by addition of a selected volume or concentration of formulation or its precursor to the environment or in contact with the substrate. Alternatively, contact may occur by addition, including controlled addition of the substrate to the formulation or a precursor thereof.

Contact may be combined with stirring or other agitation, with scrubbing, scraping or other abrasive method if appropriate for the environment and/or substrate. Contact may be combined with removal precipitant or other solids present or formed in the environment or on contact with the substrate. The environment or substrate may be pre-treated prior to contact. The treated environment to substrate may be subject to another form of cleaning or disinfection.

Figure 4:
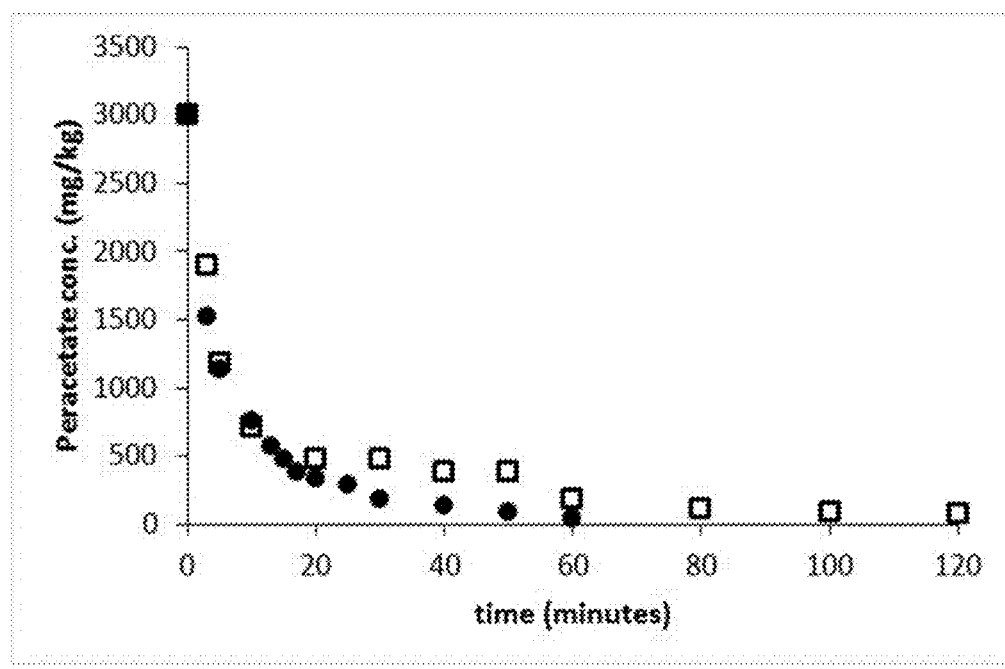
FIG. 4 is a graphical representation of peracetate concentration over time at 50° C. in clean water (open squares) and 5% pulp solids (solid circles).

Referring now to an exemplary ethanol production system 100 as shown in FIG. 4 for illustrative purposes, represents a variety of fermentation processes resulting in ethanol production as well as by products of the fermentation process.

In some embodiments, peracetate oxidant solution is used for microbial disinfection of a fermentation feedstock prior to a fermentation process. The peracetate oxidant solution is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and active oxidant is eliminated before entering the fermentation stage containing, for example, engineered microbes.

For example, a guar gum dispersion in water was tested for microbial disinfection and preservation with sodium peracetate solution. Guar gum dispersions were made in 150 mL glass jars with air tight covers by dissolving/dispersing 0.60 grams of food grade guar gum in 60 mL of distilled water containing 0.60 g of sodium chloride to make 1% guar dispersions. The dispersions were heated in a water bath to 30° C. for 45 minutes to hydrate the guar. A first jar sample was cooled to room temperature and held as the control sample. The viscosity of the room temperature guar dispersion was similar to warm honey. A second jar sample was spiked with about 130 mg/L dose of sodium peracetate and mixed thoroughly. The temperature was maintained at 30° C. for 60 minutes and then cooled to room temperature. The viscosity of the second sample appeared very similar to the first. Within 24 hours of preparation the first, control sample had a significant loss of viscosity while the second, treated sample remained visibly unchanged. After seven days the first, control sample had microbial growth visible as a biofilm developing on the surface of the liquid while the second, treated sample remained visibly unchanged.

Peracetate oxidant solution is compatible with stainless steel and has a very low corrosion rate on copper. It has low volatility allowing it to remain in solution at elevated temperatures for improved efficiency and eliminates exposure of personnel to chlorine or chlorine dioxide vapors. Peracetate oxidant has very low halogenated byproduct formation potential making it safer for cleaning and sanitizing food contact surfaces (no toxic halogenated residues) and preventing discharge of halogenated oxidation and disinfection byproducts. Because of these attributes peracetate oxidant can be safely used in higher concentrations than hypochlorite, chlorine dioxide and ozone for sanitization.

In some embodiments, vapor corrosion tests reflecting vapor corrosion conditions potentially encountered in hot environments such as the vapor head space in closed tanks and pipes and in open-air paper making processes and their facilities were also conducted. Vapor corrosion is a particular problem in industrial processing where structural steel supports and other equipment is degraded and must be replaced periodically due to long-term exposure to corrosive vapors. These tests compare continuous exposure to vapor-phase concentrations of peracetate oxidant, chlorine bleach, chlorine dioxide and peracetic acid in the head space above oxidant solutions in sealed containers. Saturated oxygen from air was used as a control test for the corrosion rate of just the carrier fluid in air. Measured corrosion rates in the vapor phase are reduced significantly using peracetate oxidant relative to bleach, chlorine dioxide and peracetic acid. The low volatility of peracetate oxidant solution (peracetate oxidant is a solid in its native form) minimizes vapor corrosion and odors from the oxidant. This behavior is in contrast to elemental chlorine, chlorine dioxide and ozone, which are gasses with very limited solubility in water at elevated temperatures, and peracetic acid, which is significantly volatile.

Vapor corrosion tests were conducted with test coupons suspended in the vapor head space in closed containers over a period of 6 hours, which was long enough to provide accurate weight loss measurements while monitoring oxidant concentration. Oxidant concentration was monitored hourly and additional oxidant was added to the carrier fluid during the test period as needed. On steel the peracetate oxidant was about 1.7 times more corrosive than air, chlorine bleach was about 8.6 times more corrosive than air, chlorine dioxide was about 11 times more corrosive than air and peracetic acid was about 5 times more corrosive than air (peracetic acid consisted of a 1:1.3 mass ratio of PAA to $H_2O_2$ in acetic acid and water).

In some embodiments, transport and storage of peracetate oxidant solutions is avoided by its generation from stable feedstocks at or near the point of use. The small amount of peracetate present on site is produced in water at dilute concentrations (less than 8%) thereby avoiding hazards associated with highly concentrated or pure oxidant materials and minimizing fugitive air emissions and worker exposure to harmful materials, VOCs or nuisance odors. Potential fugitive air emissions from the peracetate oxidant solution production process are a small amount of water vapor and oxygen gas. The produced peracetate oxidant solution concentrate is dispensed by means of a pump, eductor or other engineered conveyance device that transfers the liquid product in a contained system to the point of use. The peracetate oxidant solution is produced as needed on site and on demand thereby eliminating storage and handling of large quantities of the oxidant product material on site.

In some embodiments, peracetate oxidant solutions have the ability to reduce corrosion in fermentation process serving to protect the integrity of pulp slurries, coating ingredients, whitewater loop, and process equipment. Controlling sessile bacteria helps to prevent the accumulation of biofilm deposits which cause microbiologically influenced corrosion (i.e., biocorrosion).

Figure 5:
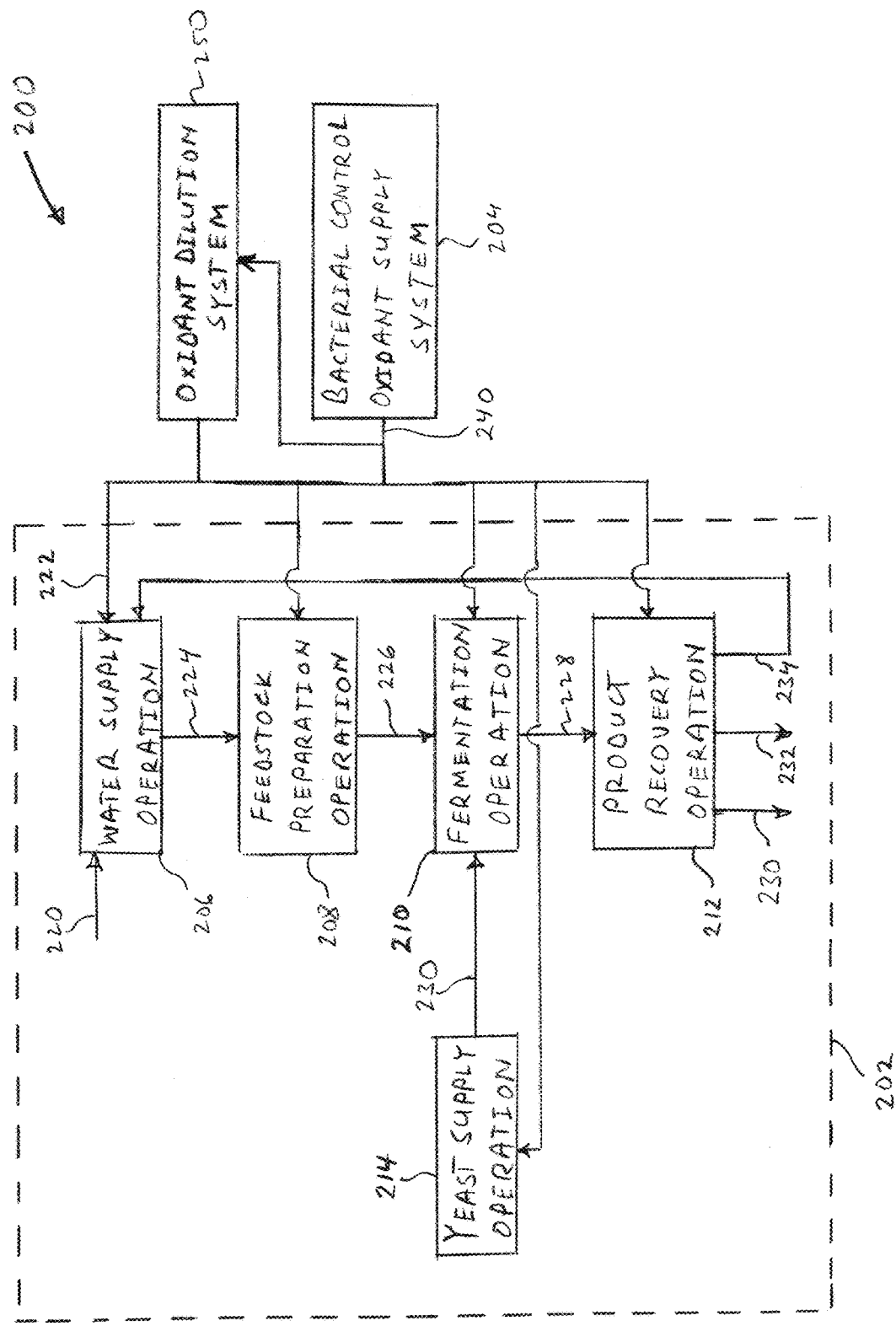
FIG. 5 is an illustration of an example yeast fermentation system for processing biomass feedstock to prepare an alcohol product and with chemical oxidant bacterial control using peracetate oxidant solution.

Reference is now made to FIG. 5, showing an illustration of an example of a yeast fermentation system 200 for fermentation processing of biomass feedstock to prepare an alcohol product and with chemical oxidant bacterial control. The illustrated yeast fermentation system 200 includes an alcohol production system 202 to prepare an alcohol product from biomass feedstock and a bacterial control oxidant supply system 204 in fluid communication with the alcohol production system 202 to supply a peracetate oxidant solution for delivery to the alcohol production system for introduction into process liquid at various illustrated example locations. The alcohol production system 202 is illustrated for production of ethanol as the desired alcohol product, however such a system could also be adapted for production of other alcohol product (e.g., butanol). The alcohol production system 202 includes a plurality of fluidly-connected operations, including a water supply operation 206, a feedstock preparation operation 208, a fermentation operation 210, a product recovery operation 212 and a yeast supply operation 214. Each of these operations includes equipment for fluid processing to perform the identified operation, wherein such equipment may include, for example, fluid containment vessels (e.g., tanks), pumps, valves, mixers, filters, centrifuges, cyclones and/or other fluid containment or processing equipment, with equipment interconnected with appropriate flow conduction conduits for communication of fluid streams within and between the operations.

As illustrated in FIG. 5, the water supply operation 206 is supplied with fresh make-up water 220 and recycle water 222 which are combined as needed and processed to prepare feed water 224 for use as aqueous process liquid in the processing performed within the alcohol production system 202. The feedstock preparation operation 208 receives and processes biomass feedstock containing sugar, starch and/or sugars useful in the preparation of the alcohol product. The feedstock preparation operation 208 includes equipment to handle the biomass feedstock (e.g., hoppers, conveyors) and to break down the biomass feedstock to an appropriate form, such as in small pieces, (e.g., milling, grinding, chopping and/or pulverizing equipment) as well as any equipment and reagents appropriate for the feedstock to convert cellulose and/or starch (polysaccharide) to sugars and to prepare a sugar-containing feed 226 containing such sugars in process liquid for processing in the fermentation operation 210. The feedstock preparation operation 208 may, for example, include equipment for performing any of the pretreatment and/or hydrolysis as discussed with respect to FIG. 1, depending upon the particular biomass feedstock to be processed.

In the fermentation operation 210, the sugar-containing feed 226 is subjected to fermentation in a fermenter to produce the desired alcohol. The sugar-containing feed 226 may be introduced into the fermenter to become part of and processed by fermentation in an active fermentation mixture including yeast. The fermenter may be provided in the form of any appropriate bioreactor system for performing fermentation with yeast. Yeast for use in the fermentation operation 210 may be supplied as needed in a yeast feed 230 from the yeast supply operation 214. The yeast supply operation 214 may, for example, include equipment and supplies for preparing a starter culture of yeast, and propagating the yeast, typically under aerobic conditions, to prepare the yeast feed 230. A raw fermentation product 228 recovered from the fermentation operation 210 includes the desired alcohol, ethanol in this example, produced during fermentation in the fermenter. The raw fermentation product 228 will be comprised mostly of aqueous process liquid (e.g., water) with a smaller quantity of alcohol and biomass feedstock residue (e.g. distiller grains) and byproducts, and including byproducts from peracetate oxidant of the peracetate oxidant solution used for bacterial control. (e.g., acetate and glycols). In the example product recovery operation 212 illustrated in FIG. 5, the raw fermentation product 228 is separated into a purified alcohol product 230, distillers dried grains with solubles (DDGS) 232 and effluent water 234. As shown in FIG. 5, effluent water 234 may be recycled (with appropriate water treatment and periodic bleed as needed for the particular application) for reuse in the water supply operation 206 to provide additional feed water for use in further operation of the alcohol production system 202.

As shown in FIG. 5, the bacterial control oxidant supply system 204 is operative to supply a peracetate oxidant solution 240 for delivery to the alcohol production system 202 for introduction into process liquid at one or more available locations in the alcohol production system 202. The peracetate oxidant solution 240 as supplied from the bacterial control oxidant supply operation 204 may include a combination of any of the properties described elsewhere in this disclosure (e.g., pH in a range of from pH 10 to pH 12, and containing either no hydrogen peroxide or hydrogen peroxide at a molar ratio of peracetate to hydrogen peroxide of greater than 16:1). Because the peracetate oxidant solution 240 is a non-equilibrium composition at an alkaline pH at which the composition is highly active, the composition of the peracetate oxidant solution 240 will change with time and the pH will naturally decline with time. Accordingly, it is generally preferred that the peracetate oxidant solution be prepared in the bacterial control oxidant supply system 204 and following such preparation is delivered to and used in the alcohol production system 202 within a short timeframe, for example as discussed elsewhere in this disclosure. The bacterial control oxidant supply system 204 may include appropriate equipment and supplies to prepare and supply the peracetate oxidant solution 240 as needed for use on a continuous or periodic basis in the alcohol production system 202. The oxidant supply system 204 may include precursors (e.g., hydrogen peroxide, sodium hydroxide, acetyl donor) for preparation of the peracetate oxidant solution 240 and appropriate equipment for combining and mixing such precursors to prepare the peracetate oxidant solution 240. Such precursors may be contained within the bacterial control oxidant supply system 204 in appropriate storage containers and precise metering and control of quantities and proportions of such precursors combined to prepare the peracetate oxidant solution 240 may be provided within the bacterial control oxidant supply system 204 by appropriate (e.g., flow control valves, metering pumps, electronic controller processing instructions and controlling operation of flow control equipment for preparing the peracetate oxidant solution 240).

As shown in FIG. 5, the peracetate oxidant solution 240 may be delivered to the alcohol production system 202 for use without further processing or may the diluted in an oxidant dilution system 250 prior to delivery to the alcohol production system 202 for use. The bacterial control oxidant supply system 204 may have its own supply of make-up water for use to prepare the peracetate oxidant solution 240 or may use water provided by the water supply operation 206. Likewise, the oxidant diluent system 250 may have its own supply of make-up water or may use water provided by the water supply operation 206 for use to dilute the peracetate oxidant solution prior to delivery to the alcohol production system 202. In the example yeast fermentation system 200 illustrated in FIG. 5, the bacterial control oxidant supply system 204 is fluidly connected to optionally deliver peracetate oxidant solution 242 multiple different locations in the alcohol production system 202 where the peracetate oxidant solution 240 may be introduced into aqueous process liquid of various streams within the alcohol production system 202. As shown in FIG. 5, water supply operation 206, the feedstock preparation operation 208, the fermentation operation 210, the product recovery operation 212 and the yeast supply operation 214 each includes at least one such location where the peracetate oxidant solution may be utilized for introduction into aqueous process liquid for bacterial control at various points within the alcohol production system 202.

All peracetate oxidant test formulations in the following examples, as initially prepared, have pH in a range of from pH 10 to pH 12, more typically pH 10.4 to pH 10.8, and a molar ratio of peracetate to hydrogen peroxide of greater than 16:1. All references to peracetate oxidant doses in these examples and elsewhere in this disclosure are to concentrations, relative to the composition being treated, and are expressed as values measured as peracetate acid

EXAMPLES

Having now described the invention, the same will be more readily understood through reference to the following example(s), which are provided by way of illustration, and are not intended to be limiting of the present invention.

Example 1: Disinfection of a Fermentation Feedstock

Sodium peracetate oxidant was used for bacterial reduction of polysaccharide feedstock materials used for producing succinic acid and lactic acid in a fermentation process. The peracetate is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and oxidant residual is eliminated before entering the fermentation stage containing the engineered microbes.

The thermally activated peracetate treatment is conducted for 30 to 90 minutes depending on the oxidant consumption rate, solids loading and particle size of the feedstock materials. The level of residual active oxidant can be monitored by ORP or by a peroxide titration method. The ORP of the active oxidant mixture can exceed 700 mV (vs SHE) during treatment while the ORP will drop significantly when the oxidant has been consumed, for example, to less than 500 mV.

After antimicrobial treatment the feedstock materials are fed to the fermenter along with other nutrients, pH buffers or additives necessary to support the fermentation process. The byproducts of the peracetate formulation, including acetate and glycerol, are readily fermented in the fermentation process and do not need to be washed or separated from the disinfected feedstock materials. After fermentation the chemical products (succinic and lactic acid) are separated from the fermentation broth, refined and purified.

Example 2: Microbial Control of a Fermentation Feedstock

Sodium peracetate oxidant was used for microbial disinfection of a corn grist. Corn was crushed in a hammer mill to powder form and was rehydrated for 30 minutes with water to a 30% wt/wt mixture while heating to 75° C. A 5.8% sodium peracetate solution is blended with this mixture in the suction side of a slurry transfer pump to make an initial sodium peracetate concentration of about 50 mg/kg.

The thermally activated peracetate disinfection treatment is conducted for about 5 minutes until the active oxidant is consumed. The rate of oxidant consumption may be monitored by ORP. During peracetate oxidant treatment the ORP of the grist may exceed 750 mV vs SHE. An ORP of about 520 mV (vs SHE) or less indicates that the active oxidant is consumed. The concentration of residual active oxidant may also be measured directly using a standard iodometric peroxide titration method.

After the peracetate-ROS treatment, the feedstock materials are fed to liquefaction vessels and the remainder of the ethanol production process is conducted normally with other nutrients, pH buffers, enzymes, yeast and other additives necessary to support the fermentation process. The byproducts of the peracetate formulation, including acetate and glycerol, may be consumed in the fermentation process.

After fermentation, the ethanol is distilled from the fermentation broth or stillage. Residual acetate and glycerol are retained in the stillage.

Example 3: Sequential Dosing of Peracetate Oxidant

Sequential, lower concentration
doses of the peracetate oxidant can be more effective against bacteria than a single, high concentration dose. This behavior can be used to reduce the impact of the oxidant on yeast while selectively killing bacteria contaminating a fermenter.

A mixed produced water sample that originated from the Piceance basin in CO, USA contained suspended and dissolved solids, anaerobic bacteria and up to about 1.5% salinity. This sample was used to test the difference between dosing multiple quantities of oxidant and dosing a single quantity equivalent to the sum of the multiple doses. The test procedure was as follows: 50 or 100 mL of thoroughly mixed produced water sample was dispensed into a 250 mL beaker with magnetic stir bar. A high sodium pH electrode and an ORP electrode were suspended in the produced water for continuous measurement at room temperature. Oxidant solution was added to the produced water while stirring at a moderate rate. ATP concentration measurements (Luminultra Technologies) were made periodically to monitor microbial activity.

Figure 2:
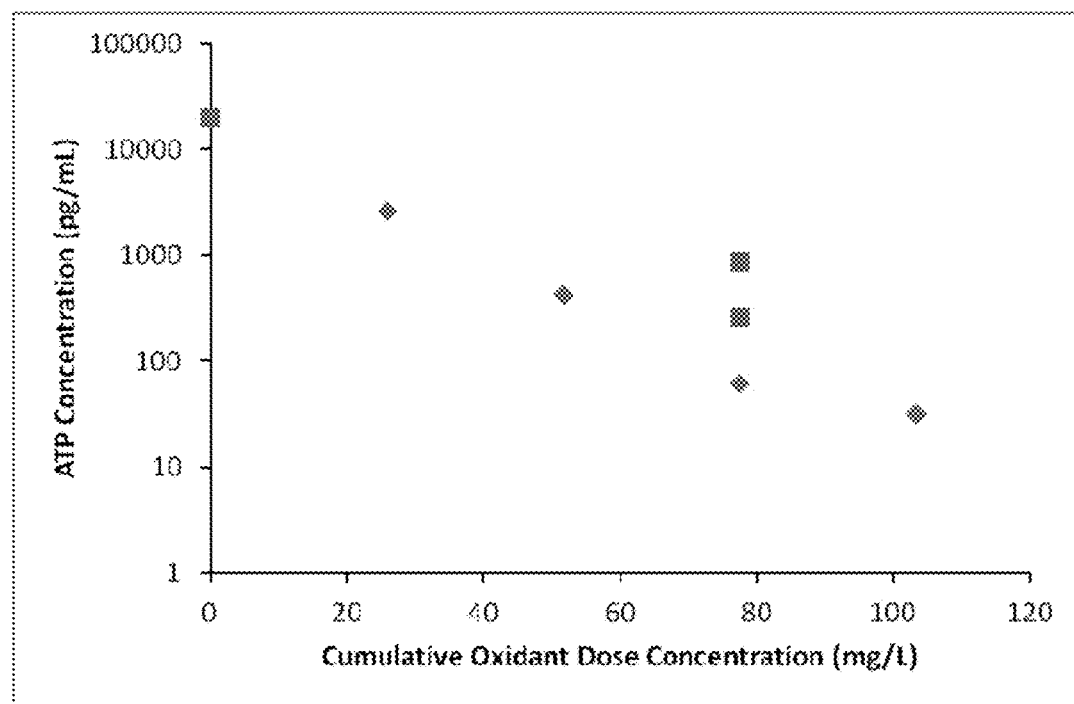
FIG. 2 is a graphical representation of the reduction of ATP concentration after each sodium peracetate oxidant dose. Diamonds are sequential additions of oxidant and ATP measured at 15 min contact time after each 26 mg/L dose; squares are a single oxidant dose equal to 78 mg/L and ATP measured at 15 and 30 minute contact times.
Figure 3:
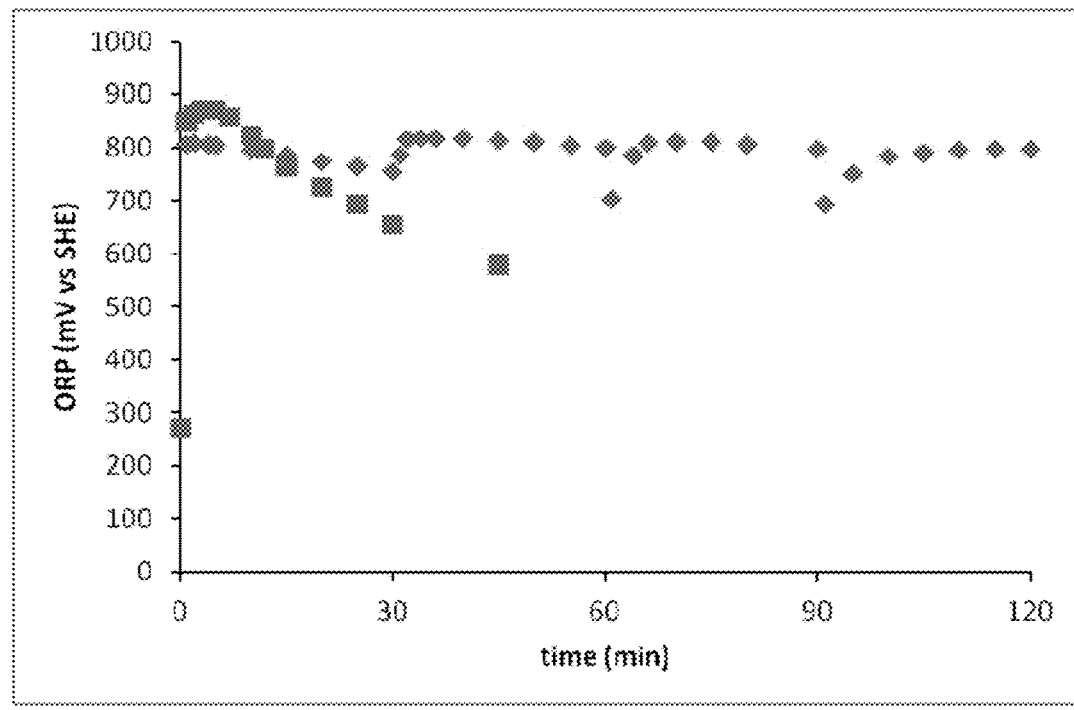
FIG. 3 is a graphical representation depicting ORP of produced water treated with sodium peracetate oxidant, diamonds are the response to sequential additions of oxidant at 0, 30, 60 and 90 minutes; squares are the response to a single oxidant dose.

For the sequential oxidant dosing treatment, each sodium peracetate oxidant dose concentration was 26 mg/L (20 mg/L measured as peracetate). The first oxidant dose was added and the ORP rapidly increased to more than 800 mV vs SHE. The ATP concentration was measured at 15 minutes contact time after each dose of oxidant was added. Each subsequent quantity of oxidant was dosed into the water after 30 minutes of contact time with the previous oxidant dose. A total of four oxidant doses were made and the results are provided in FIG. 2 and FIG. 3. The ATP concentration results in FIG. 2 show a logarithmic decrease over the first three oxidant additions and less benefit from the fourth addition. The ORP response in FIG. 3 shows a small decrease after each of the first two additions. Upon the third and fourth additions the ORP spiked down and then recovered to a more sustained level. The downward spike in ORP is thought to be due to the fresh oxidant reacting with the reactive species responsible for the activated, elevated ORP. The ORP recovers as more reactive, high ORP species are produced by oxidant activation in the contaminated water.

For the single oxidant dose treatment, the sodium peracetate oxidant dose concentration was 78 mg/L (60 mg/L as peracetate). The first oxidant dose was added and the ORP rapidly increased to a maximum of 870 mV vs SHE then decreased continuously over time as shown in FIG. 3. The ATP concentration was measured at 15 and 30 minutes contact time after the oxidant was added. The ATP concentration in the produced water treated with a single dose was significantly greater than the ATP concentration in the water treated with sequential doses with the same cumulative dose concentration. The ORP of the sequentially-dosed water was sustained at a high value compared to the single dose treated water where the ORP decreased to below 600 mV vs SHE in less than 60 minutes, which is more favorable for killing bacteria.

Example 4: Bactericidal Control in a Fermenter with Sequential Dosing of Peracetate Oxidant A barley fermentation grist containing about 30% solids by weight at a pH of 5.5 to 6.5, 30° C. was about 30% way through its fermentation period. A 5.8% sodium peracetate solution was injected into the grist as it entered a pump used to circulate the fermenter's contents. A first dose of peracetate solution was added to provide about a 20 mg/kg dose of oxidant. The grist's ORP was monitored and showed an initial increase, then decrease after 3-4 minutes. About 5 minutes after the first oxidant dose was added, a second 20 mg/kg dose of oxidant was added. About 5 minutes after the second oxidant dose was added, a third 20 mg/kg oxidant dose was added. About 10 minutes after the third oxidant dose the ORP had returned to normal fermentation conditions.

Example 5: Corrosion Testing

The corrosivity of the peracetate oxidant formulation to metal alloys is similar to dissolved oxygen in water and generally less corrosive than chlorine and chlorine dioxide chemistries as demonstrated with side-by-side comparative tests on corrosion coupons. The following corrosion tests were conducted at room temperature (22-24° C.) for two week exposure periods. Corrosion rates are reported in mils/year (mpy). Solutions were made from dechlorinated tap water containing 1% NaCl. Corrosion tests were conducted using the following procedure. Standard corrosion coupons (Metal Samples Company) with 120 grit sanded finish were mounted in a 0.75" pipe diameter corrosion loop assembled in a standard "bypass piping system" configuration. The test solution was circulated at a rate of about 0.75 gpm through the corrosion loop (laminar flow conditions). Test solutions were maintained at a constant composition during the corrosion test period with a constant makeup of fresh solution into a circulation reservoir with an overflow outlet. Oxidant concentrations in the reservoir were verified at least twice daily. Coupon corrosion rates were evaluated following the procedural guidelines of ASTM-G1. New coupons were used in each test and were washed with alcohol and air dried prior to weighing and testing. Coupons were dried and loose material brushed off with a plastic scrub pad, rinsed and air dried prior to weighing. Mass of coupons was measured to the nearest 0.0001±0.0003 g.

TABLE 1

| Alloy | Dissolved Oxygen 8-9 ppm | Peracetate Oxidant 10 ppm | Chlorine Dioxide 10 ppm |
|---|---|---|---|
| Carbon steels | | | |
| C1018 | 27.65 | 33.080 | 44.66 |
| Ductile | 34.02 | 34.46 | 53.22 |
| pipe L80 | 37 | | 37.50 |
| Stainless Steels | | | |
| CA6NM | 0.97 | 0.62 | 4.83 |
| 17-4 PH | 0.000 | 0.29 | 3.55 |
| 304L | 0.08 | 0.03 | 2.02 |
| CD4MCUN | 0.10 | 0.01 | 0.01 |
| Other Materials | | | |
| Al 6061 | 9.52 | 9.15 | 13.2 |
| CDA122 | 4.56 | 8.87 | 7.39 |

Chlorine dioxide caused significant pitting overall compared with little to no pitting for peracetate oxidant and dissolved oxygen. Localized pit corrosion was observed under many of the Nylon coupon mounting screws for all oxidants, which skewed results to higher values on otherwise pristine coupons. In general, 1% salt increased corrosivity of the test solutions, sometimes significantly, over fresh water. Peracetate oxidant concentrations of 35 and 45 ppm gave nearly the same results as for 10 ppm on the stainless steel alloys and water pipe copper alloy, CDA 122 (pure copper was virtually unaffected).

Corrosion tests were conducted using the following procedure. Standard corrosion coupons (Metal Samples Company) with 120 grit sanded finish were mounted in a 0.75" pipe diameter corrosion loop assembled in a standard "bypass piping system" configuration. The test solution was circulated at a rate of about 0.75 gpm through the corrosion loop (laminar flow conditions). Test solutions were maintained at a constant composition during the corrosion test period with a constant makeup of fresh solution into a circulation reservoir with an overflow outlet. Oxidant concentrations in the reservoir were verified at least twice daily. Coupon corrosion rates were evaluated following the procedural guidelines of ASTM-G1. New coupons were used in each test and were washed with alcohol and air dried prior to weighing and testing. Coupons were dried and loose material brushed off with a plastic scrub pad, rinsed and air dried prior to weighing. Mass of coupons was measured to the nearest 0.0001±0.0003 g.

Example 6: TOX Formation Tests in Pulp Bleaching

The potential of organic halide formation during pulp bleaching was compared between peracetate oxidant solution, peracetic acid and chlorine dioxide at 50° C. and 5% pulp consistency. The pulp slurries were prepared in distilled water containing 1.0% sodium chloride to simulate salt accumulation in a bleaching circuit, which can contribute to the formation of free chlorine and chlorinated byproducts in the presence of oxidizing bleaching chemicals. The pulp slurries were prepared by weighing out 45.0 g of 50 lb Kraft paper (Pacon Corp.), cutting the paper into smaller pieces (about 1 square inch), wetting the paper in 650-750 mL of distilled water containing 1.0% NaCl and pulping the mixture in a blender for about 2-3 minutes until the consistency was approximately uniform. The pulp slurry was put into a 1 L glass beaker in a heated water bath. The beakers were fitted with liquid-tight covers to minimize evaporative losses of water and oxidants. After the pulp slurry was heated the oxidant solution and additional salt water was added to make a final composition of about 855 g water, 45.0 g of air-dry pulp, 8.55 g NaCl and the oxidant. The oxidant was mixed into the pulp slurry thoroughly with a stainless steel spatula for several minutes and then mixed periodically throughout the 2 hour bleaching period. The pH of the slurry was left at the natural pH created by each oxidant in the presence of the pulp.

The amount of oxidant used in each test was enough to partially bleach the amount of lignin present so that the oxidant was the limiting reagent. When peracetate oxidant was combined with Kraft pulp the evolution of some gas was observed accompanied by rapid bleaching that was clearly visible within the first few minutes. Chlorine dioxide also bleached the pulp rapidly, but to a lesser extent because it was applied at a lower concentration due to its limited solubility and high volatility. Peracetic acid produced a large amount of gas, but was least effective at bleaching. After 2 hours at 50° C. the pulp slurries were vacuum filtered through a Buchner funnel over a medium porosity filter paper. There was no residual oxidant present in the filtrates. The four filtrate solutions recovered were put into amber glass bottles and preserved with sulfuric acid for total organic halide analyses, which were conducted by a third party laboratory.

Each of the filtrate water solutions had a different color. The filtrate from chlorine dioxide was the darkest orange, the peracetate oxidant filtrate was light yellow, the peracetic acid filtrate was pale yellow and the blank's filtrate was golden-yellow.

Peracetate oxidant formed the least amount of TOX under the bleaching conditions. Normalizing the TOX formation to the concentration of oxidant used, the peracetate oxidant formed about 2.7 times less TOX than peracetic acid and about 10.4 times less TOX than chlorine dioxide. The peracetate oxidant solution provides strong bleaching performance and greatly reduced organic halide oxidation byproduct formation potential compared to conventional bleaching agents. The peracetate oxidant can significantly reduce pollution caused by the formation of halogenated oxidation byproducts.

TABLE 2

| Oxidant | Initial Oxidant Concentration (mg/L) | TOX (mg/L) | Normalized TOX (mg/L per 1000 mg/L oxidant) |
| --- | --- | --- | --- |
| Blank | 0 | 0.68 | — |
| Peracetate oxidant solution | 4000 (as PAA equivalents) | 6.7 | 1.7 |
| Peracetic Acid | 4000 (PAA), 5400 ($H_2O_2$) | 17.8 | 4.5 |
| Chlorine Dioxide | 1000 | 17.7 | 17.7 |

Example 7: Peracetate Consumption Rates in Water Vs High Organic Loading

Measurement of peracetate concentration over time was conducted in clean tap water and in 5% consistency hardwood pulp at 70° C., which is a common temperature for pulp delignification and bleaching processes in a paper mill. In a first test a 250 mL solution of tap water containing an initial peracetate concentration of 3000 mg/L at 70° C. was made by mixing 37.5 mL of a 2.0% wt/vol solution of the peracetate formulation concentrate (made at room temperature) into 212.5 mL of tap water already heated to 70° C. in a 1 L glass beaker in a hot water bath. Samples were removed for analysis at regular time intervals and the results presented in FIG. 4, open squares represent the tap water samples. The initial pH was 9.0 and the final pH was 5.8. The initial ORP was 540 mV vs SHE, which increased to a maximum of 785 mV in 30 minutes.

In a second test a 250 mL slurry of a north American hard wood pulp fiber (16.0 kappa number) at 5% consistency and 70° C. containing an initial peracetate concentration of 3000 mg/L was made by mixing 37.5 mL of a 2.0% wt/vol solution of the peracetate formulation concentrate (made at room temperature) into 200 mL of tap water with 12.5 g (oven dry weight) of pulp fiber already heated to 70° C. in a 1 L glass beaker in a hot water bath. The slurry was thoroughly mixed and samples of the oxidant liquor were removed and filtered for analysis at regular time intervals. The results are presented in FIG. 4 solid circles represent the pulp slurry samples. The initial pH was 8.8 and the final pH was 6.4. The initial ORP was 675 mV vs SHE, which increased to a maximum of 850 mV in 25 minutes. The peracetate concentration decreased at a similar rate for both tests over the first 10-20 minutes. After about 20 minutes the residual peracetate concentration in tap water persisted longer at a higher concentration than the residual in the pulp slurry. At 30 minutes the peracetate residual in tap water was about 9.6% higher than the residual in the pulp slurry relative to the initial peracetate concentration.

Example 8: The Use of Peracetate Oxidant in Combination with a Conventional Biocide A produced water with bacteria population that had entered the more difficult-to-treat stationary phase was used as the treatment challenge. ATP and bug bottles were used to evaluate efficacy after a 40 minute total contact time. Table 3 shows the benefit of using peracetate oxidant with didodecyldimethylammonium bromide (DDAB).

TABLE 3

| Product | Dose (mg/L) | Contact Time (min) | ATP (pg/mL) | APB (bottles) | SRB (bottles) |
|---|---|---|---|---|---|
| Blank | 0 | — | 2790 | ≥7 | ≥7 |
| Peracetate oxidant | 20 | 40 | 200 | 2 | 3 |
| DDAB | 10 | 40 | 185 | 3 | 5 |
| DDAB | 5 | 40 | 291 | 4 | 6 |
| Peracetate oxidant then DDAB | 15 5 | 20 20 | 82 | 0 | 1 |

ATP measurements under-reported bacteria (possibly by a factor of 10) in the low-growth stationary phase in the untreated water. High bug bottle counts for DDAB, even with reduced ATP, suggest that DDAB was less effective against bacteria in the stationary phase than peracetate oxidant.

Example 9: Bioethanol Plant Treatment Tests

Impacts of peracetate oxidant solution were tested on fermentation in a bioethanol plant in lab tests at the facility. These tests were used to determine the impact of peracetate oxidant solution on yeast activity, enzyme activity and ethanol production metrics in a clean (very low bacteria/antibiotic-treated) fermentation stage. Bacteria control was evaluated in the raw mash (prior to adding yeast and antibiotic).

In summary, peracetate oxidant solution had no detrimental impacts on ethanol production and enzyme activity at a treatment dose of 60 ppm or less. Yeast cell counts were the same while viability and budding increased with increasing peracetate oxidant solution treatment dose. Bacteria control was demonstrated by treatment of the raw mash after allowing propagation of native yeast and bacteria.

Fermentation Mash Tests:

Mash was removed from the fermenter about 6 hours into fermentation during the fermenter filling process from the yeast propagation stage. The mash contained yeast, nutrient and antibiotic. Eleven, 250-gram samples of mash were added to 500 mL Erlenmeyer flasks outfitted with Teflon coated magnetic stir bars and fermentation locks filled with mineral oil. Three of the samples were controls (no treatment) and four concentrations of peracetate oxidant solution were tested in duplicate.

Peracetate oxidant solution was freshly made as a 2.0% wt/vol solution (measured as peracetic acid) and aliquots added to each test sample (at about 28-30° C.) while stirring rapidly by hand with an ORP sensor probe. Peracetate oxidant solution doses were added with initial target concentrations of 30, 60, 90 and 120 mg/kg (mg oxidant measured as peracetic acid per kg of mash). The control and test sample flasks were place in a heated water bath with magnetic stirrers. Fermentation temperature of the samples were maintained on the same temperature and time program as the main fermenter in the plant (about 50 hours fermentation). Samples were measured for weight loss, yeast activity and final composition parameters. Results are summarized in Table 4.

TABLE 4

Parameter Response Trends with Increasing Peracetate Oxidant Dose:

| | |
|---|---|
| Total Average Yeast Cell Count | No change |
| Viability (%) | Increasing |
| Budding (%) | Increasing |
| Weight Loss (g) | No change |
| DP4+ (%) | No change |
| DP3 (%) | No change |
| Maltose (%) | No change |
| Glucose (%) | No change up to 60 ppm, decreased at higher doses |
| Fructose (%) | No change relative to fermenter in plant, but control read zero |
| Lactic Acid (%) | No change (may be higher at 120 ppm dose) |
| Acetic Acid (%) | No change (may be higher at 120 ppm dose) |
| Glycerol (%) | Increasing |
| Ethanol (%) | Minimal/no change up to 60 ppm, decreasing at higher doses |

Yeast Activity

Figure 6:
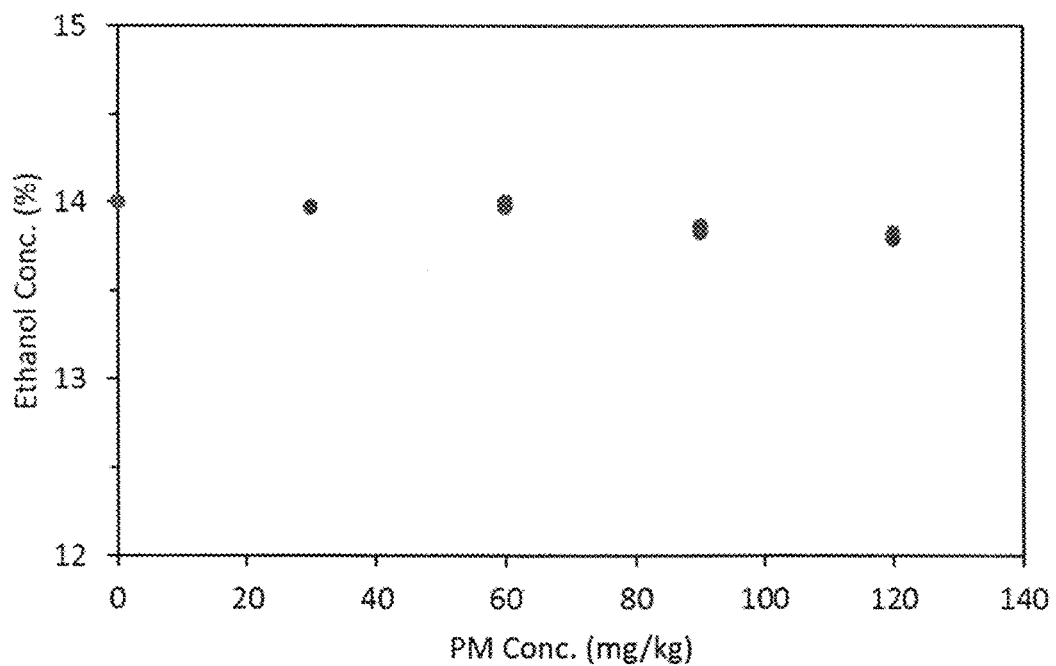
FIG. 6 is a graphical representation of ethanol concentration vs. initial dose concentration of peracetate oxidant solution in Example 9.
Figure 7:
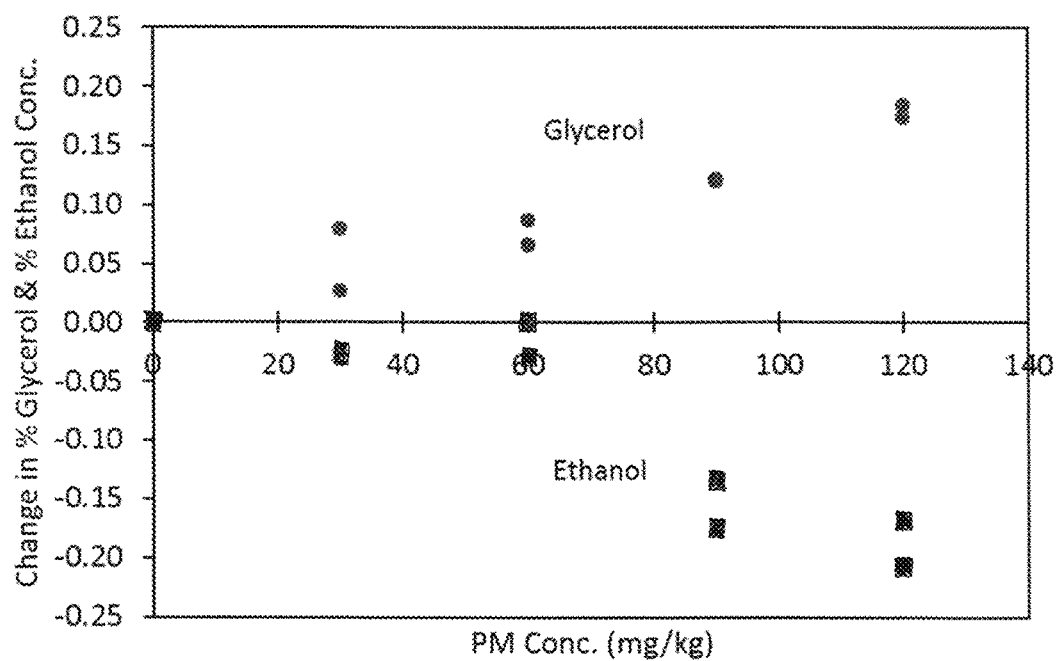
FIG. 7 is a graphical representation of changes in glycerol and ethanol concentrations vs. initial dose concentration of peracetate oxidant solution in Example 9.

The impact of peracetate oxidant solution on ethanol production was minimal at 60 ppm initial dose and lower as illustrated in FIG. 6, which shows ethanol concentration after fermentation of test samples treated with peracetate oxidant solution. The changes in composition of glycerol and ethanol relative to the untreated "control" after fermentation of test samples treated with peracetate oxidant solution are shown in FIG. 7. Glycerol production increased slightly with increasing peracetate oxidant dose (measured as peracetic acid), but a decrease in ethanol concentration was not observed until 90 and 120 ppm peracetate oxidant doses were used.

Oxidative or chemical stress on yeast can increase glycerol production significantly (e.g., up to 300%). At 120 ppm Peracetate oxidant solution, glycerol increased about 30% over the control. A general rule-of-thumb is that glycerol production occurs at the expense of ethanol production in approximately a 2:1 mass ratio. That relationship is not being followed by these results. The time-frame in which excess glycerol production occurred was not determined (i.e., during yeast propagation phase, fast fermentation/production phase, slow fermentation).

Figure 8:
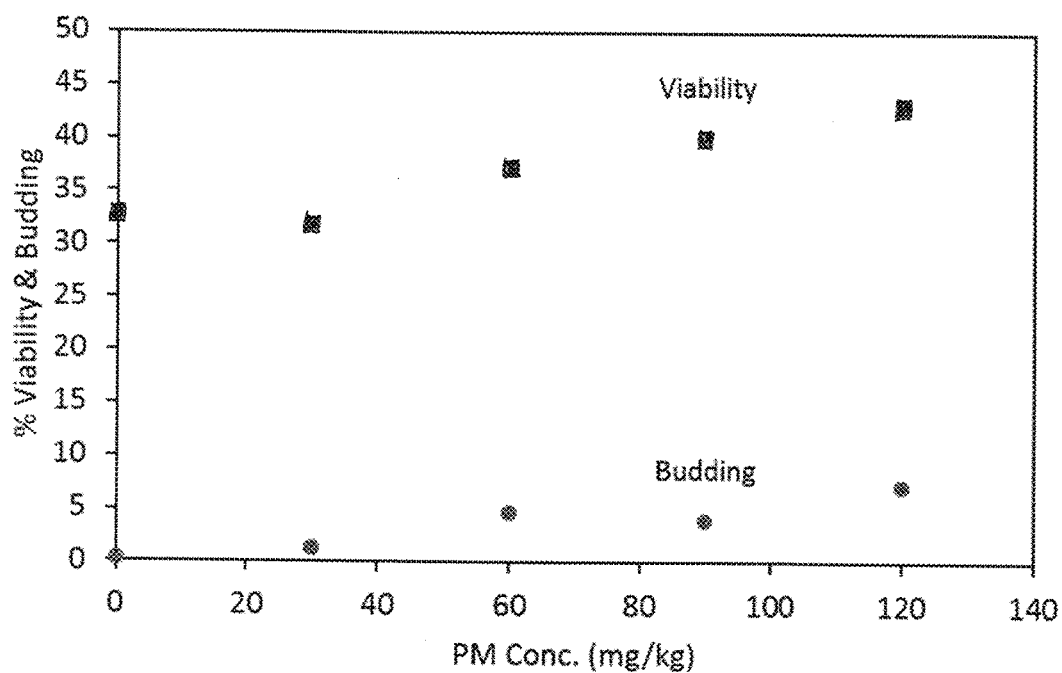
FIG. 8 is a graphical representation of percent viability and budding of yeast cells vs. vs. initial dose concentration of peracetate oxidant solution in Example 9.

Yeast cell counts after fermentation were unaffected by treatments. The percent viability and budding of yeast cells generally increased with increasing peracetate oxidant solution above 30 ppm treatment dose as shown in FIG. 8, which shows yeast viability and budding after fermentation of test samples treated with peracetate oxidant solution.

Enzyme Activity

Simultaneous saccharification and fermentation (SSF) is the process used by the ethanol production facility. Treatment of the fermentation mash with peracetate oxidant solution had no impact on enzyme activity based on there being no change in DP4+ (dextrin) and DP3 (maltotrios) residual saccharides concentrations relative to the untreated "control" sample after fermentation. Maintaining constant glucose, fructose and ethanol concentrations with up to 60 ppm peracetate oxidant solution dose is also consistent with no loss of enzyme activity or significant changes in yeast activity.

ORP Response

Figure 9:
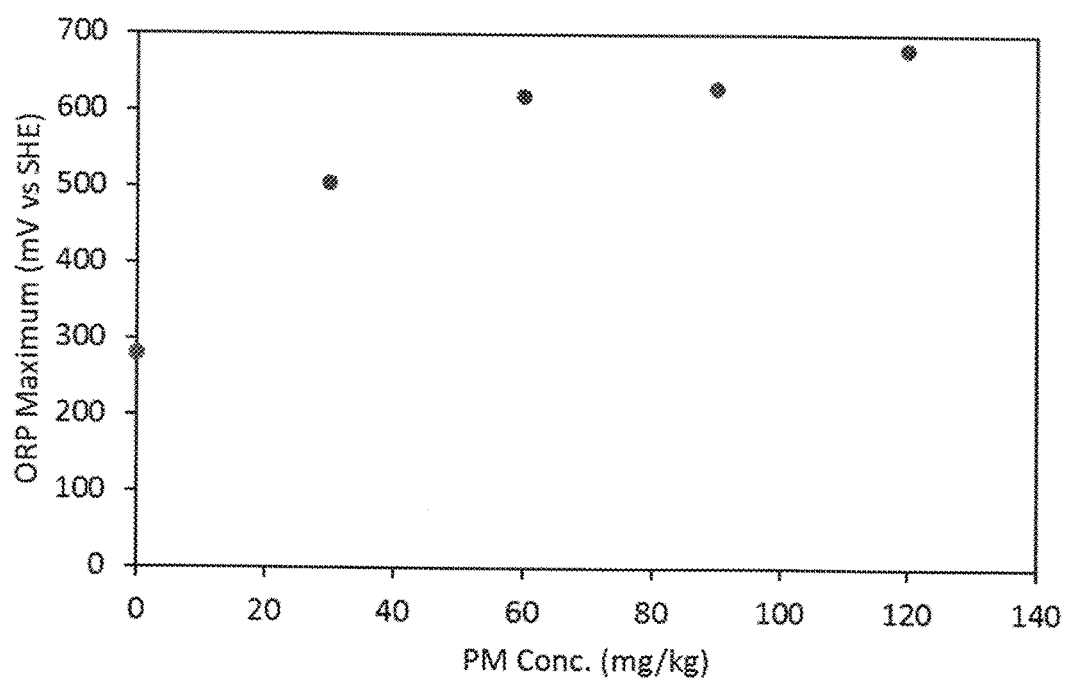
FIG. 9 is a graphical representation of maximum ORP of fermentation mash vs. vs. initial dose concentration of peracetate oxidant solution in Example 9.

ORP spiked during initial addition/mixing of peracetate oxidant solution and rapidly decreased over 5 minutes. By 30 min ORP was slightly greater than the initial, pre-dose level. The approximate maximum ORP observed during initial mixing showed an increasing trend, as shown in FIG. 9, which shows maximum ORP of fermentation mash while mixing in peracetate oxidant solution treatment doses.

Example 10: Evaluation of Bacteria Control in Mash

Raw mash (prior to addition of yeast or antibiotic in the fermentation mash used in the above tests) was evaluated for total microbial activity before and after 60 ppm oxidative microbial treatments. A reduction of microbial activity primarily represents the reduction in bacteria because yeast are not significantly affected at this treatment level. The total microbial response to peracetate oxidant solution (PAO) was compared to that of chlorine dioxide ($ClO_2$) and peracetic acid (PAA). The use of $ClO_2$ at 30-55 ppm doses for bacteria control has already been established in bioethanol fermentation processes as an alternative to antibiotics. The performance of peracetate oxidant solution was demonstrated to be very similar to $ClO_2$ and PAA.

The raw mash was first allowed to ferment with its native microbial population (yeast and bacteria) at room temperature for about 65 hours. Fermentation was active as shown by significant $CO_2$ evolution and by a significant decrease in pH from pH 5.57 to 4.17. 50 g portions of the fermented mash were treated with 60 ppm peracetate oxidant solution, 60 ppm $ClO_2$ and 67 ppm PAA (with 45 ppm $H_2O_2$). After oxidants were mixed into the mash samples they were left to stand at room temperature in covered flasks (not air tight) during the analysis period. Optical microscope evaluation of the liquid phase showed a mixture of microbial populations including Saccharomyes cerevisiae and Schizosaccharomyces pombe (based on morphological differences of observed cells).

Total microbial activity was evaluated by measuring the cellular metabolite adenosine triphosphate (ATP) concentration in 0.50 g samples of mash using the LifeCheck ATP Sessile Kit and Photon Master luminometer (Luminultra). ATP concentration is reported as pg/g of mash. The ATP concentration of the raw mash was 778,900 pg/g (standard deviation was ±5% of the reported value). After 65 hours fermentation at room temperature, prior to treatment, ATP was 6,305,000 pg/mL showing about a 10-fold increase in microbial activity or population.

Figure 10:
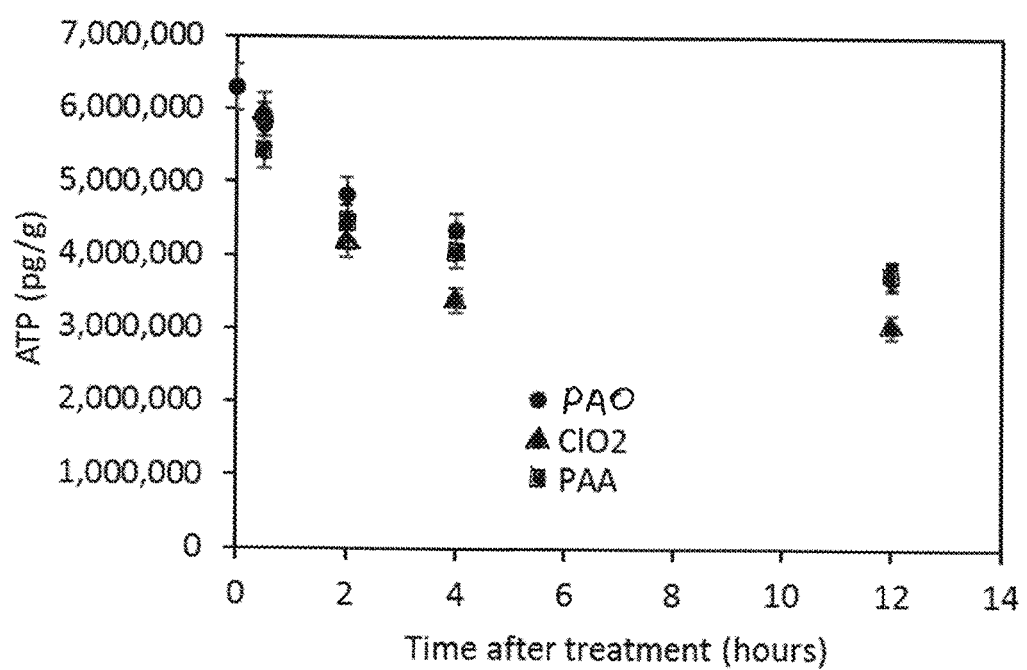
FIG. 10 is a graphical representation of ATP concentration over time in Example 10.

All three oxidants reduced ATP over time on a similar curve over time as shown in FIG. 10, which shows ATP concentration over time after treatment of fermented mash with 60 ppm oxidant doses. Reduction of ATP over time is typical for many bacteria species (anaerobic and aerobic) treated with these oxidants in the presence of other materials, which often cause cellular damage followed by cell death in the first 2-24 hours after treatment. Peracetate oxidant solution treatment reduced ATP by almost 40% at 4 hours after treatment indicating that a significant fraction of microbial activity was acid-producing bacteria, consistent with the significant pH reduction during fermentation.

Separate analyses of the raw mash (before fermentation) treated with peracetate oxidant solution and $ClO_2$ at 90 and 120 ppm doses provided greater yeast activity than the untreated mash. In this comparison the raw mash was treated with oxidants and samples of the liquid phase were filtered off after 30 minutes of contact time. 1 mL aliquots were added to 9 mL anaerobic acid producing cell culture broth bottles with acid pH indicating dye. Filtrates from the oxidant-treated mash samples cultured very rapidly compared to the untreated mash. Optical microscope analysis of the cell culture broths showed that the treated mash samples contained high densities of active yeast cells (e.g., Saccharomyes cerevisiae and Schizosaccharomyces pombe) and were accompanied by gas evolution. In contrast, no yeast cells were visible in untreated mash culture broths and virtually no gas evolution was observed, however, the culture media pH was decreasing, indicating the presence of some acid-forming microbial activity.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having a feature that" performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

The entire contents of each U.S. patent and each U.S. patent application identified herein are incorporated herein by reference for all purposes. The text of such U.S. patents, U.S. patent applications, and other materials incorporated herein by reference is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for preparing a yeast culture for use in yeast fermentation processing to produce an alcohol product, the method comprising:
   culturing yeast in a culture mixture including a liquid-containing culture medium to multiply the yeast and prepare an active yeast culture for introduction into a fermenter to produce the alcohol product;
   introducing a peracetate oxidant solution into the liquid of the culture mixture for bacterial control, wherein prior to introduction into liquid of the culture mixture during the introducing, the peracetate oxidant solution comprises the following properties:
   a pH in a range of from pH 10 to pH 12; and
   either no hydrogen peroxide or hydrogen peroxide at a molar ratio of peracetate to hydrogen peroxide of greater than 16:1
   prior to the introducing, preparing the peracetate oxidant solution with the properties, comprising mixing alkaline hydrogen peroxide solution with an acyl donor at a molar excess of acyl donor reactive groups to hydrogen peroxide with a molar ratio of acyl donor reactive groups to hydrogen peroxide of at least 1.25:1.

2. The method of claim 1, wherein at the time of the introducing, the culture mixture is in a yeast propagation phase under aerobic conditions.

3. The method of claim 1, wherein the culture mixture is at a pH in a range of pH 4.5 to pH 6 during the introducing.

4. The method of claim 3, wherein the temperature of the culture mixture is in a range of from 20° C. to 50° C. during the introducing.

5. The method of claim 1, wherein the introducing comprises adding the peracetate oxidant solution into the culture mixture to provide a concentration of peracetate, measured as peracetate acid, in a range of from 20 ppm to 100 ppm.

6. The method of claim 5, comprising after the introducing, adding the yeast culture to a fermenter and conducting fermentation in the fermenter to produce an alcohol.

7. The method of claim 6, comprising adding a sugar-containing feed, separate from the yeast culture, to the fermenter.

8. The method of claim 7, comprising recovering from the fermenter a raw fermentation product comprising alcohol produced during the fermentation.

9. The method of claim 7, comprising treating the sugar containing feed with a second peracetate oxidant solution prior to the adding the sugar-containing feed to the fermenter, wherein the second peracetate oxidant solution comprises the following properties:
   a pH in a range of from pH 10 to pH 12; and
   either no hydrogen peroxide or hydrogen peroxide at a molar ratio of peracetate to hydrogen peroxide of greater than 16:1.

10. The method of claim 1, comprising reducing bacteria populations present in the yeast culture as a consequence of the introducing while maintaining yeast cellular defense mechanisms in the culture mixture.

11. The method of claim 1, wherein the introducing comprises sequentially introducing multiple doses of the peracetate oxidant solution into the liquid of the culture mixture, reducing the impact of oxidation on yeast in the culture mixture.

12. The method of claim 1, comprising increasing yeast budding in the culture mixture as a consequence of the introducing.

* * * * *